United States Patent [19]

Ong et al.

[11] Patent Number: 5,298,626
[45] Date of Patent: * Mar. 29, 1994

[54] SELECT CYCLOPENT[B]INDOLES

[75] Inventors: Helen H. Ong, Whippany, N.J.; Gerard J. O'Malley, Newtown; Michael C. Merriman, Hellertown, both of Pa.; Mark G. Palermo, Piscataway, N.J.

[73] Assignee: Hoechst-Roussel Pharmaceuticals Incorporated, Somerville, N.J.

[ * ] Notice: The portion of the term of this patent subsequent to Mar. 9, 2010 has been disclaimed.

[21] Appl. No.: 976,067

[22] Filed: Nov. 13, 1992

Related U.S. Application Data

[60] Division of Ser. No. 818,703, Jan. 9, 1992, Pat. No. 5,192,789, which is a continuation-in-part of Ser. No. 642,952, Jan. 18, 1991, Pat. No. 5,100,891.

[51] Int. Cl.$^5$ .......................................... C07D 209/80
[52] U.S. Cl. ................................................... 548/439
[58] Field of Search ......................................... 548/439

[56] References Cited

U.S. PATENT DOCUMENTS

| | | |
|---|---|---|
| 3,514,462 | 5/1970 | Hester . |
| 3,595,874 | 7/1971 | Hester . |
| 3,655,647 | 4/1972 | Hester . |
| 3,959,309 | 5/1976 | Mooradian . |
| 4,128,560 | 12/1978 | Asselin . |
| 4,172,834 | 10/1979 | Mooradian . |
| 4,224,335 | 9/1980 | Mooradian . |
| 4,343,812 | 8/1982 | Fliedner . |
| 5,100,891 | 3/1992 | Ong et al. ............... 548/439 |

FOREIGN PATENT DOCUMENTS 0482086 3/1976 U.S.S.R. .

OTHER PUBLICATIONS

Elks, J. Chem. Soc., 1944, 624–625.
Jennings, J. Chem. Soc., 1957, 497–498.
Renson, Bull. Sec. Chim. Belg., 68, 258–269 (1959).
Maryanoff, J. Org. Chem., 46, 355–360 (1981).
Mattson, J. Org. Chem., 55, 2552–2554 (1990).
Akalaeva et al., Khim–Farm Zh., 23(3), 299–302 (1989), See CA 111, 49967v (1989).
Filitis et al., Khim–Farm Zh., 22(10), 1217–1222 (1988), See CA 110, 54362c (1988).
Bokanov et al., Khim Geterotsikl Seedin, (12), 1632–1635 (1987), See CA 109, 37795h (1988).
Khvostenko et al., Khim–Farm. Zh., 1983, 17(10), 1215–1222, See CA 100, 241n (1984).
Andreeva et al., Khim–Farm, Zh. 1976, 10(11), 46–49, See CA 87, 47919t (1977).
Aiura et al., Heterocycles, 1974, 2(3), 319–322.
Shvedov et al., Khim–Farm Zh., 10(4), 22–24 (1976), See CA 85, 108475c (1976).
De Jong et al., J. Org. Chem, 37, 3571–3577 (1972).
Nagarajan et al., Indian J. Chem., 1969, 7(4), 319–322.
Gazengel et al., Chem. Pharm. Bull., 37, 1500–1503 (1989).
Castagnino et al., J. Chem. Res. Synop, 1990, (1), 30–31.
Shioiri et al., Chem. Pharm. Bull., 15(7), 1010–1014, (1967).

Primary Examiner—Robert W. Ramsuer
Attorney, Agent, or Firm—Tatsuya Ikeda

[57] ABSTRACT

There are disclosed various compounds of the formula below,

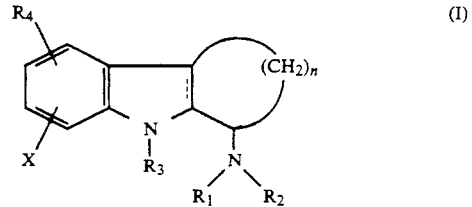

(I)

wherein n, X and $R_1$ through $R_4$ are as defined in the specification, which are useful for alleviating various memory dysfunctions characterized by a cholinergic deficit such as Alzheimer's disease.

Compounds of this invention also inhibit monoamine oxidase and/or act at central $\alpha_2$-adrenergic receptors, and hence are useful as antidepressants.

3 Claims, No Drawings

SELECT CYCLOPENT[B]INDOLES

This is a division of a prior application Ser. No. 818,703 filed Jan. 9, 1992, now U.S. Pat. No. 5,192,789, which is a continuation-in-part of a prior application, Ser. No. 642,952, filed Jan. 18, 1991, now U.S. Pat. No. 5,100,891

The present invention relates to compounds of the formula,

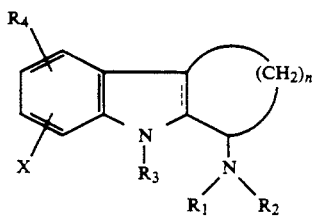

where
n is 2, 3, 4 or 5;
X is hydrogen, loweralkyl, loweralkoxy, hydroxy, halogen, trifluoromethyl or nitro;
R, is hydrogen, loweralkyl, loweralkenyl, loweralkynyl, aminoloweralkyl, loweralkylaminoloweralkyl, diloweralkylaminoloweralkyl, cycloalkyl, cycloalkylloweralkyl, cycloalkenyl, aryl, arylloweralkyl, arylcycloalkyl,

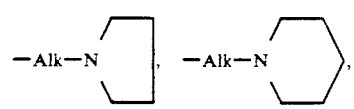

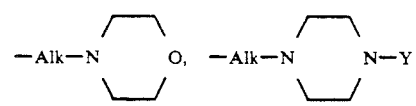

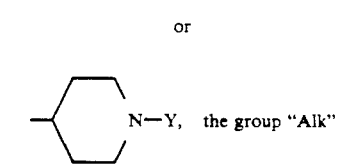

signifying a divalent loweralkylene group, and Y signifying hydrogen, loweralkyl, aryl or arylloweralkyl;
$R_2$ is hydrogen, loweralkyl, formyl, loweralkylcarbonyl, benzyloxycarbonyl or loweralkylaminocarbonyl; or alternatively,

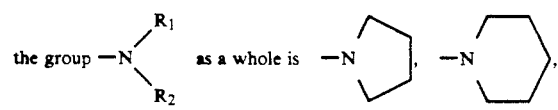

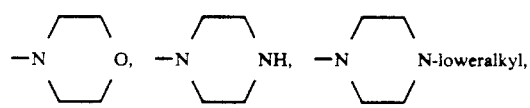

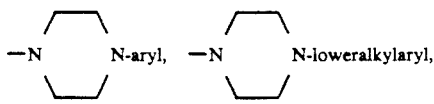

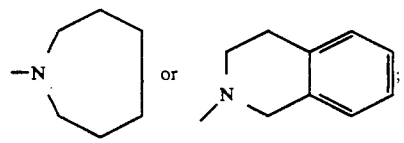

$R_3$ is hydrogen, loweralkyl, arylloweralkyl, loweralkylcarbonyl or loweralkoxycarbonyl;
$R_4$ is hydrogen, —OH,

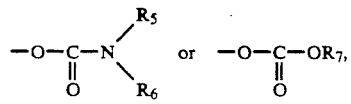

or wherein
$R_5$ is loweralkyl, loweralkenyl, loweralkynyl, cycloalkyl, cycloalkylloweralkyl, aryl, arylloweralkyl, arylcycloalkyl; and
$R_6$ is hydrogen, loweralkyl, aryl or arylloweralkyl; or alteratively

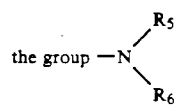

as a whole is

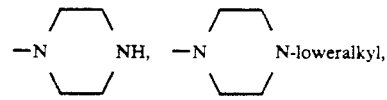

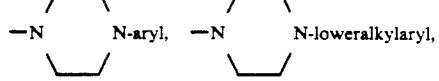

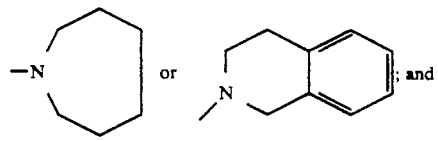

$R_7$ is loweralkyl, aryl or arylloweralkyl;
which compounds are useful for alleviating various memory dysfunctions characterized by a cholinergic deficit such as Alzheimer's disease. Compounds I of this invention also inhibit monoamine oxidase and/or act at central $\alpha_2$-adrenergic receptors, and hence are useful as antidepressants.

Also included within the scope of this invention are compounds of Formula II, where $R_3$, $R_4$, X and n are as previously defined, which are useful as direct precursors to the target compounds of this invention.

Also included within the scope of this invention are compounds of Formula III, where $R_8$ is hydroxy, aminoloweralkoxy, loweralkyl, cycloalkyl, cycloalkenyl, arylloweralkyl, arylcycloalkyl, loweralkylcarbonyloxy or loweraminocarbonyloxy; which are useful for alleviating various memory dysfunctions characterized by a cholinergic deficit such as Alzheimer's disease. Compounds III of this invention also inhibit monoamine oxidase and/or act as presynaptic ($\alpha_2$-adrenergic receptor antagonists, and hence are useful as antidepressants.

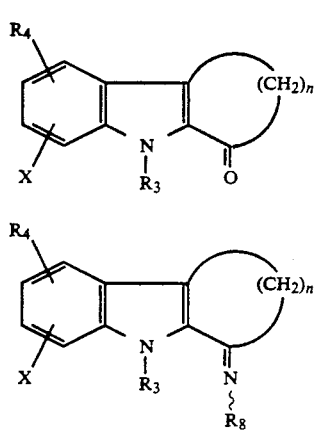

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term cycloalkyl shall mean a cycloalkyl group of 3 to 7 carbon atoms.

The term halogen shall mean fluorine, chlorine, bromine or iodine.

The term aryl shall mean a phenyl group substituted with 0, 1 or 2 substituents, each of which being independently loweralkyl, loweralkoxy, halogen, trifluoromethyl, hydroxy or nitro.

Throughout the specification and the appended claims, a given chemical formula or name shall encompass all stereo and tautomeric isomers where such isomers exist.

The compounds of this invention are prepared by utilizing one or more of the synthetic steps described below.

Throughout the description of the synthetic steps, the notations n, X, Y and $R_1$ through $R_8$ shall have the respective meanings given above unless otherwise stated or indicated.

STEP A

A compound of Formula IV, where $R_9$ is hydrogen or —OCH$_3$, is allowed to cyclize to afford a compound of Formula V. This reaction is typically conducted in aqueous sulfuric acid at a temperature of 25° to 150° C.

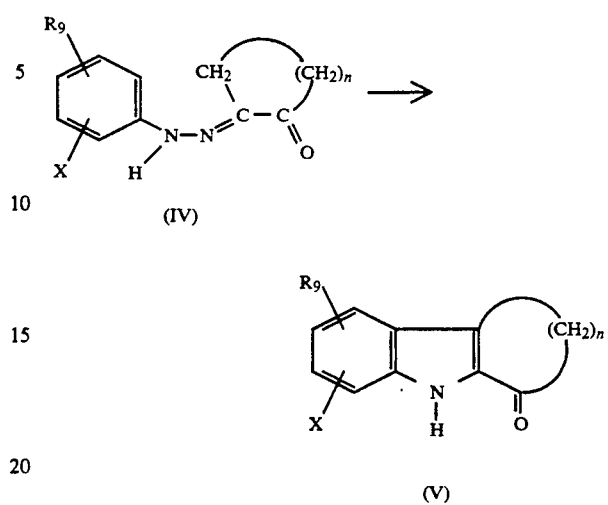

STEP B

Compound V is allowed to react with a sulfate compound of the formula, $(R_{10}O)_2SO_2$, where $R_{10}$ is loweralkyl or arylloweralkyl, in a routine manner known to the art to afford a compound of Formula VI. Alternatively, compound V is allowed to react with a halide compound of the formula $R_{10}$-Hal, where $R_{10}$ is as defined above, in a routine manner known to the art, to afford a compound of Formula VI.

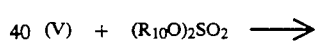

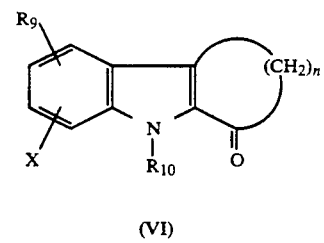

STEP C

Compound V is allowed to react with a diloweralkyl pyrocarbonate of the formula, $R_{11}$—O—CO—O—CO—O—$R_{11}$, where $R_{11}$ is a loweralkyl group, in the presence of a suitable catalyst, preferably 4-dimethylaminopyridine, to afford a compound of Formula VII.

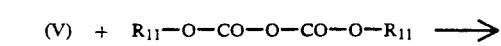

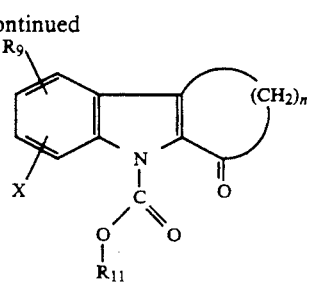

(VII)

STEP D

Compound V is allowed to react with an acyl chloride of the formula $R_{11}$—CO—Cl in a routine manner known to the art to afford a compound of Formula VIII.

(V) + $R_{11}$—CO—Cl ⟶

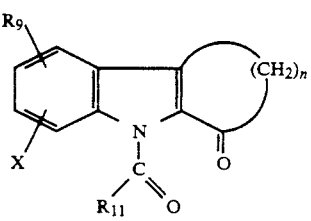

(VIII)

STEP E

A compound of Formula IX obtained from STEP B is subjected to a cleavage reaction to afford a compound of Formula X. Typically, to this end, compound IX is allowed to react with BBr$_3$/tetrahydrofuran complex and the resultant product is hydrolyzed in a routine manner known to the art.

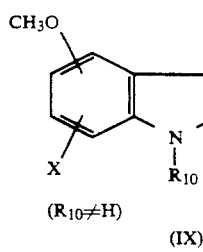

(IX) ($R_{10} \neq H$)

(X)

STEP F

As a special case, a compound of Formula XI is allowed to react with chloroacetyl chloride in the presence of aluminum chloride in a routine manner known to the art to afford a compound of Formula XII (Friedel-Crafts reaction).

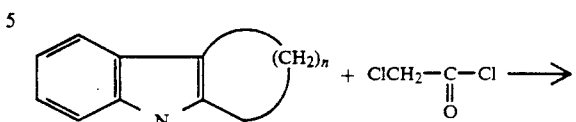

(XI)

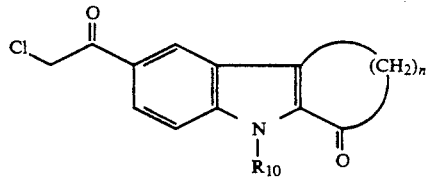

(XII)

STEP G

Compound XII is allowed to react with a peracid, preferably m-chloroperbenzoic acid in a routine manner known to the art to afford a compound of Formula XIII (Baeyer-Villiger reaction).

(XII) + peracid ⟶

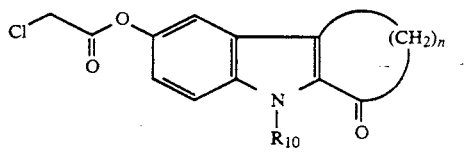

(XIII)

STEP H

Compound XIII is hydrolyzed preferably in the presence of a base such as sodium hydroxide to afford a compound of Formula XIV.

(XIII) + H$_2$O/NaOH ⟶

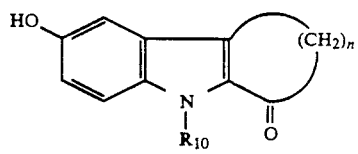

(XIV)

STEP I

A compound of Formula XV, where $R_{12}$ is hydrogen, methoxy or hydroxy, which is obtained from one of the foregoing steps is allowed to react with hydroxylamine hydrochloride in a routine manner known to the art to afford a compound of Formula XVI. Typically, this reaction is conducted by first suspending compound XV in ethanol and thereafter adding an aqueous solution of sodium acetate and an aqueous solution of hydroxylamine hydrochloride to the suspension and stirring the resultant mixture at a temperature of 25° to 1500° C.

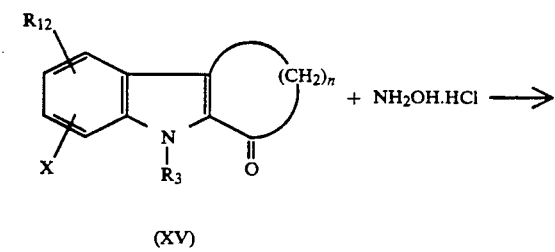

(XV)

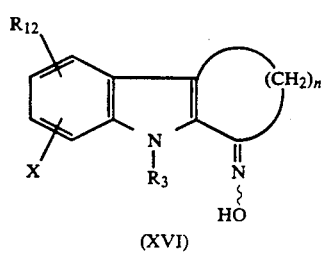

(XVI)

STEP J

Compound XVI is allowed to react with an aminoloweralkyl bromide of the formula, Br—R$_{13}$—NH$_2$, where —R$_{13}$—NH$_2$ is an aminoloweralkyl group, in a routine manner known to the art to afford a compound of Formula XVII.

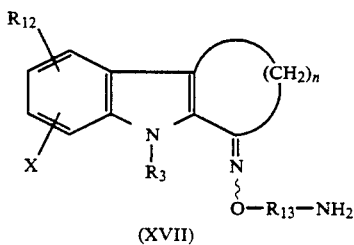

(XVII)

STEP K

Compound XV is allowed to react with a primary amine of the formula

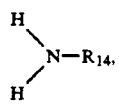

where R$_{14}$ is loweralkyl, loweralkenyl, loweralkynyl, cycloalkyl, cycloalkenyl, arylloweralkyl, arylcycloalkyl or aryl, in a routine manner known to the art to afford an imine of Formula XVIII.

It is preferable to conduct this reaction in the presence of titanium (IV) isopropoxide and a suitable solvent such as acetonitrile. Typically, this reaction is conducted at a temperature of 0° to 80° C. This method is more advantageous than a method using TiCl$_4$ or a method wherein the reaction is conducted in a sealed tube at an elevated temperature with the aid of molecular sieves used as a water removing agent.

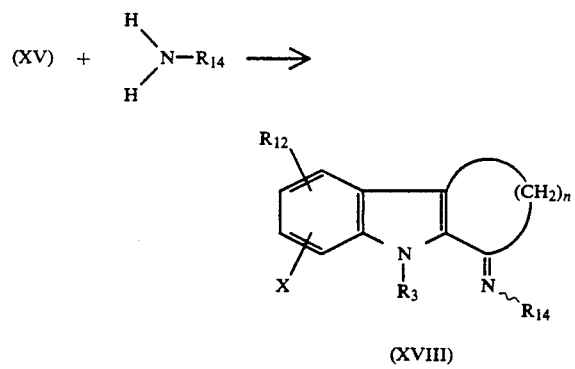

(XVIII)

STEP L

Compound XVI is reduced with the aid of a Raney alloy and a sodium hydroxide solution in a similar manner as reported by B. Staskun and T. van Es (J. Chem. Soc., C., 531 (1966)) to afford a compound of Formula XIX.

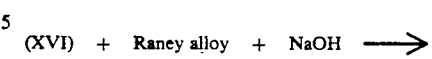

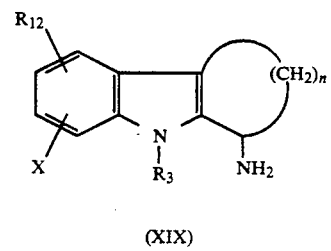

(XIX)

STEP M

Compound XV is allowed to react with titanium isopropoxide and a secondary amine of the formula

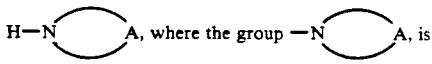

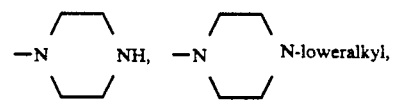

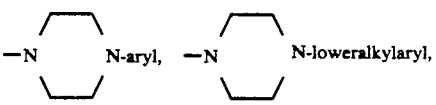

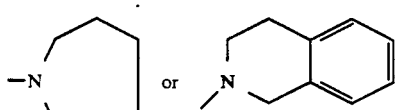

followed by reduction with sodium cyanoborohydride under conditions similar to that described by R. J. Mattson et al., J. Org. Chem., 55, 2552-4 (1990), to afford a compound of Formula XX.

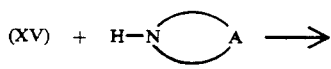

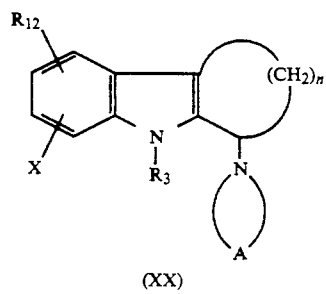

STEP N

Compound XVIII is reduced with sodium borohydride, sodium cyanoborohydride or borane/tetrahydrofuran complex in a routine manner known to the art to afford a compound of Formula XXI.

(XVIII) + NaBH₄
NaCNBH₃
or BH₃/THF  ⟶

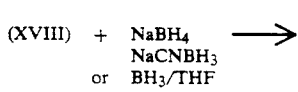

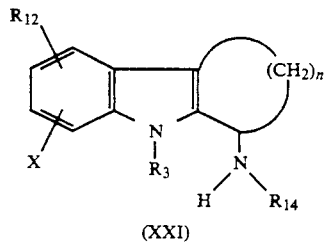

STEP O

Compound XIX is reduced with the aid of borane/tetrahydrofuran and trifluoroacetic acid complex to afford a compound of Formula XXII.

(XIX) + BH₃/THF + CF₃CO₂H  ⟶

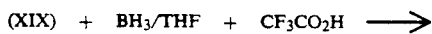

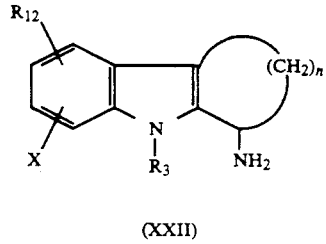

STEP P

A compound of Formula XXIII, which is obtained from STEP L or O, is allowed to react with a halide compound of the formula R₁₅-Hal where R₁₅ is loweralkyl, loweralkenyl, loweralkynyl, cycloalkylloweralkyl, arylloweralkyl,

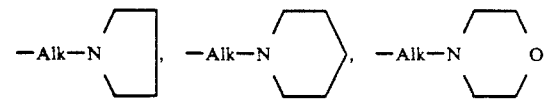

or

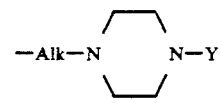

to afford a compound of Formula XXIV.

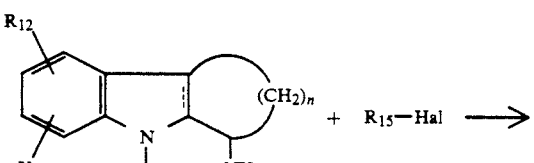

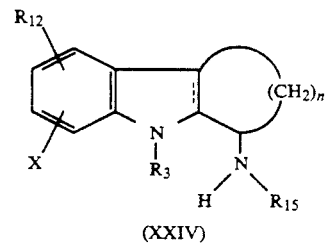

STEP Q

A compound of Formula XXV, where R₁₆ is hydrogen, loweralkyl, loweralkenyl, loweralkynyl, cycloalkyl, cycloalkenyl, arylloweralkyl or arylcycloalkyl, is allowed to react with formic acid in the presence of 1-(3-dimethylaminopropyl)-3-ethyl carbodiimide and 4-dimethylaminopyridine or the mixed anhydride prepared from formic acid and acetic anhydride to afford a compound of Formula XXVI.

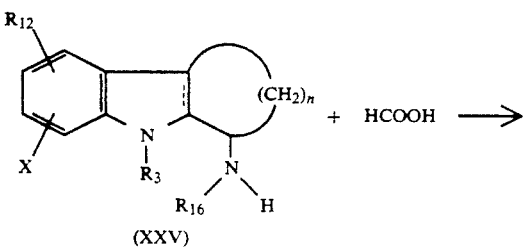

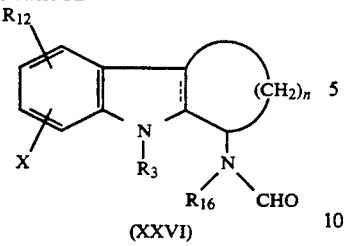

(XXVI)

STEP R

Compound XXV is allowed to react with an acyl chloride of the formula, $R_{17}$—CO—Cl, where $R_{17}$ is a loweralkyl group, in a routine manner known to the art to afford a compound of Formula XXVII.

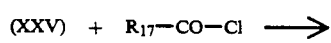

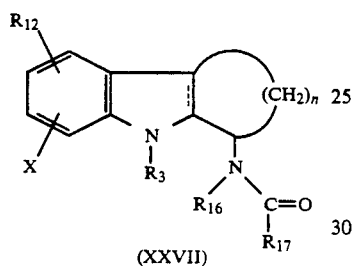

(XXVII)

STEP S

A compound of Formula XXV, where $R_{12}$ is not hydroxy, is allowed to react with a benzyl chloroformate in a routine manner known to the art to afford a compound of Formula XXVIII.

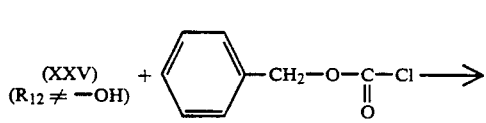

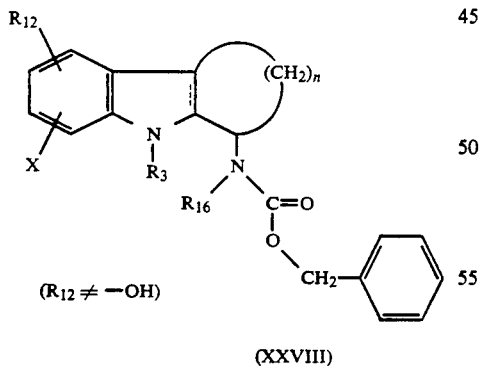

(XXVIII)

STEP T

A compound of Formula XXV, where $R_{12}$ is not hydroxy, is allowed to react with an isocyanate of the formula $R_{17}$—N=C=O, where $R_{17}$ is a loweralkyl, aryl or arylloweralkyl group, to afford a compound of Formula XXIX. Typically, this reaction is conducted in the presence of a suitable catalyst such as 1,8-diazabicyclo[5.4.0]undec-7-ene.

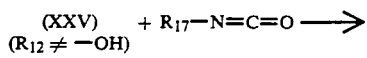

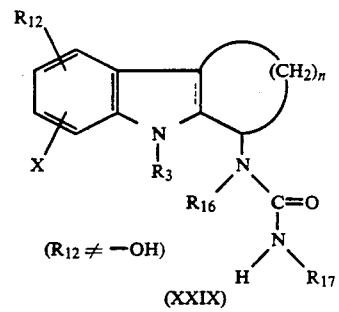

(XXIX)

STEP U

A compound of Formula XVI, where $R_{12}$ is not hydroxy, is allowed to react with an isocyanate of the formula $R_{17}$—N=C=O in substantially the same manner as in STEP T to afford a compound of Formula XXX.

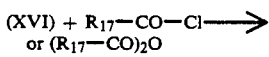

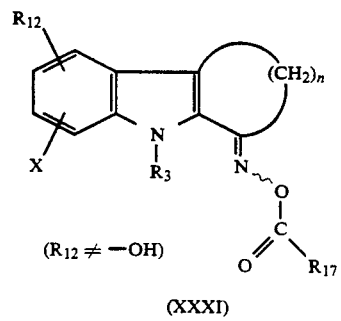

(XXX)

STEP V

Compound XVI is allowed to react with an acyl chloride of the formula $R_{17}$—CO—Cl or an acid anhydride of the formula $(R_{17}$—CO$)_2$O in a routine manner known to the art to afford a compound of Formula XXXI.

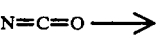

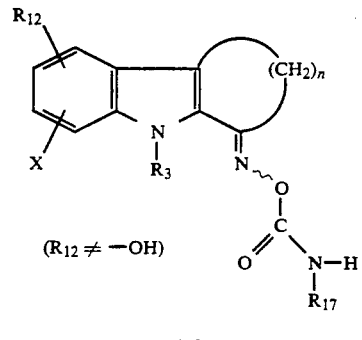

(XXXI)

STEP W

A compound of Formula XXXII, where $R_2$ is not loweralkylaminocarbonyl, which is obtained from one of the foregoing STEPS is allowed to react with a chloroformate of the formula

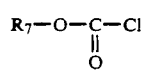

in a routine manner known to the art to afford a compound of Formula XXXIII.

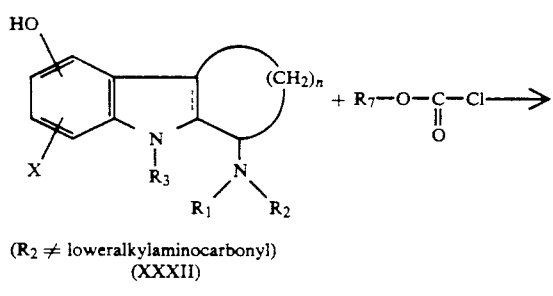

($R_2 \neq$ loweralkylaminocarbonyl)
(XXXII)

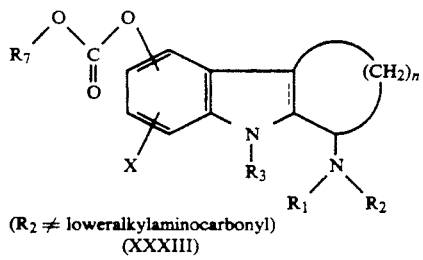

($R_2 \neq$ loweralkylaminocarbonyl)
(XXXIII)

STEP X

A compound of Formula XXXIIIa which is obtained from STEP W is allowed to react with an isocyanate of the formula $R_{17}$—N=C=O in substantially the same manner as in STEP T to afford a compound of Formula XXXIV. Subsequently, Compound XXXIV is subjected to hydrogenolysis conducted with the aid of a suitable catalyst such as palladium-carbon in a routine manner known to the art to afford a compound of Formula XXXV.

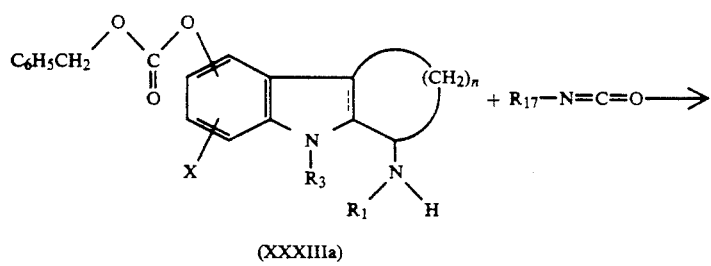

(XXXIIIa)

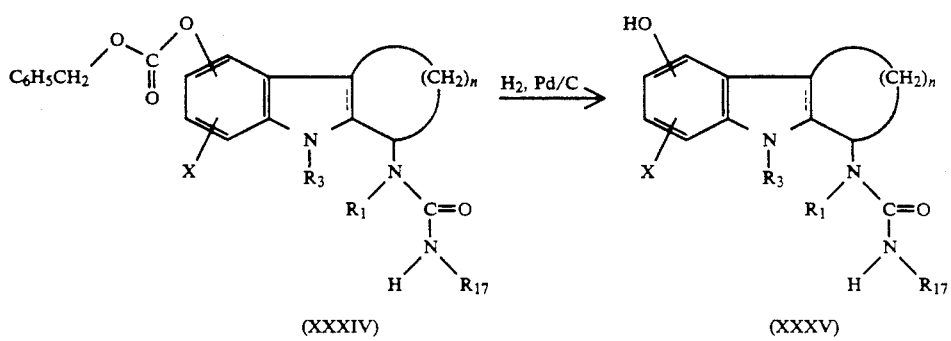

(XXXIV)                    (XXXV)

STEP Y

A compound of Formula XXXVI, which is obtained from one of the foregoing STEPS, is allowed to react with an isocyanate of the formula $R_{17}$—N=C=O in substantially the same manner as in STEP T to afford a compound of Formula XXXVII.

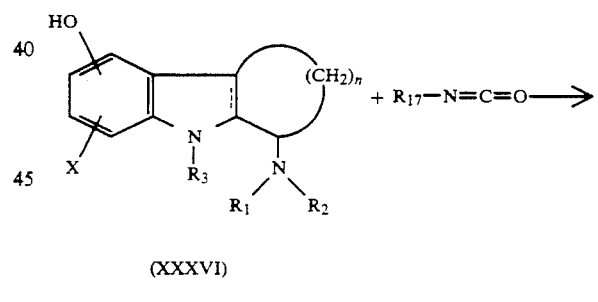

(XXXVI)

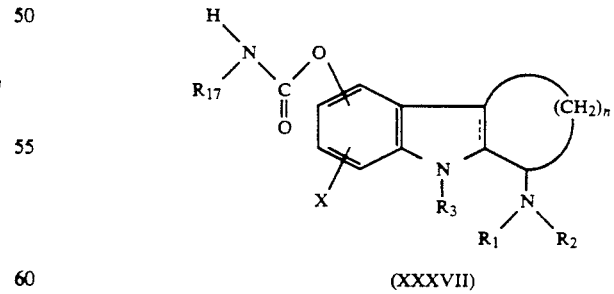

(XXXVII)

The compounds of Formula I and Formula III of the present invention are useful for the treatment of various memory dysfunctions characterized by a decreased cholinergic function such as Alzheimer's disease. Compounds of this invention also inhibit monoamine oxidase and/or act at central $\alpha_2$-adrenergic receptors and hence are useful as antidepressants.

The activity to alleviate such memory dysfunctions is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (ACHE) distribution is correlated with central cholinergic innervation. This same innervation is suggested to be weakened in Alzheimer patients. We have determined in vitro inhibition of acetylcholinesterase activity in rat striatum.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. ACHE may be distinguished from other cholinesterases by substrate and inhibitor specificities and by regional distribution. Its distribution in brain roughly correlates with cholinergic innervation and subfractionation shows the highest level in nerve terminals.

It is generally accepted that the physiological role of ACHE is the rapid hydrolysis and inactivation of acetylcholine. Inhibitors of ACHE show marked cholinomimetic effects in cholinergically-innervated effector organs and have been used therapeutically in the treatment of glaucoma, myasthenia gravis and paralytic ileus. However, recent studies have suggested that ACHE inhibitors may also be beneficial in the treatment of Alzheimer's disease.

The method described below was used in this invention for assaying cholinesterase activity. This is a modification of the method of Ellman et al., Biochem. Pharmacol. 7, 88 (1961).

Procedure

A. Reagents 1. 0.05M Phosphate buffer, pH 7.2
(a) 6.85 g $NaH_2PO_4.HO$/100 ml distilled $H_2O$
(b) 13.40 g $Na_2HPO_4.7H_2O$/100 ml distilled $H_2O$
(c) add (a) to (b) until pH reaches 7.2
(d) Dilute 1:10
2. Substrate in buffer
(a) 198 mg acetylthiocholine chloride (10 mM)
(b) q.s. to 100 ml with 0.05M phosphate buffer, pH 7.2 (reagent 1)
3. DTNB in buffer
(a) 19.8 mg 5,5-dithiobisnitrobenzoic acid (DTNB) (0.5 mM)
(b) q.s. to 100 ml with 0.05M phosphate buffer, pH 7.2 (reagent 1)
4. A 2 mM stock solution of the test drug is made up in a suitable solvent and q.s. to volume with 0.5 mM DTNB (reagent 3). Drugs are serially diluted (1: I 0) such that the final concentration (in cuvette) is $10^{-4}M$ and screened for activity. If active, $IC_{50}$ values are determined from the inhibitory activity of subsequent concentrations.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvehjem homogenizer. A 25 microliter aliquot of the homogenate is added to 1.0 milliliter vehicle or various concentrations of the test drug and preincubated for 10 minutes at 37° C.

C. Assay

Enzyme activity is measured with the Beckman DU-50 spectrophotometer. This method can be used for $IC_{50}$ determinations and for measuring kinetic constants.

Instrument Settings

Kinetics Soft-Pac Module #598273 (10)
Program #6 Kindata:
Source—Vis
Wavelength—412 nm
Sipper—none
Cuvettes—2 ml cuvettes using auto 6-sampler
Blank—1 for each substrate concentration
Interval time—15 seconds (15 or 30 seconds for kinetics)
Total time—5 minutes (5 or 10 minutes for kinetics)
Plot—yes
Span—autoscale
Slope—increasing
Results—yes (gives slope)
Factor—I Reagents are added to the blank and sample cuvettes as follows:
Blank: 0.8 ml Phosphate Buffer/DTNB, 0.8 ml Buffer/Substrate.
Control: 0.8 ml Phosphate Buffer/DTNB/Enzyme, 0.8 ml Phosphate Buffer/Substrate.
0.8 ml Phosphate Buffer/DTNB/Drug/Enzyme, 0.8 ml Phosphate Buffer/Substrate.

Blank values are determined for each run to control for non-enzymatic hydrolysis of substrate and these values are automatically subtracted by the kindata program available on kinetics soft-pac module. This program also calculates the rate of absorbance change for each cuvette.

For $IC_{50}$ Determinations

Substrate concentration is 10 mM diluted 1:2 in assay yielding final concentration of 5 mM. DTNB concentration is 0.5 mM yielding 0.25 mM final concentration.

$$\% \text{ Inhibition} = \frac{\text{slope control} - \text{slope drug}}{\text{slope control}} \times 100$$

$IC_{50}$ values are calculated from log-probit analysis

Results of this assay for some of the compounds of this invention and physostigmine (reference compound) are presented in Table 1.

TABLE 1

| Compound | Inhibitory Concentration, $IC_{50}$ (μM) Brain AChE |
|---|---|
| 3-(N-cyclopropyl)amino-4-methyl-1,2,3,4-tetrahydrocyclopent[b]-indol-7-yl methylcarbamate | 3.5 |
| 4-methyl-3-phenylmethylamino-1,2,3,4-tetrahydrocyclopent[b]-indol-7-yl methylcarbamate | 1.1 |
| 4-methyl-3-phenylmethylamino-1,2,3,4-tetrahydrocyclopent[b]-indol-7-yl methylcarbamate | 6.2 |

TABLE 1-continued

| Compound | Inhibitory Concentration, IC$_{50}$ ($\mu$M) Brain AChE |
|---|---|
| Physostigmine | 0.006 |

This utility is further demonstrated by the ability of these compounds to restore cholinergically deficient memory in the Dark Avoidance Assay described below.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

Results of this assay for some of the compounds of this invention and those for tacrine and pilocarpine (reference compounds) are presented in Table 2.

TABLE 2

| Compound | Dose (mg/kg of body weight, s.c) | % of Animals with Scopolamine Induced Memory Deficit Reversal |
|---|---|---|
| 3-(N-cyclopropyl)amino-4-methyl-1,2,3,4-tetrahydro-cyclopent[b]indol-7-yl methylcarbamate | 0.63 | 27% |
|  | 2.5 | 33% |
| Tacrine | 0.63 | 13% |
| Pilocarpine | 5.0 | 13% |

The utility is further demonstrated by the ability of these compounds to inhibit the enzyme monoamine oxidase, increase the brain levels of biogenic amine(s), and act as antidepressants.

Inhibition of Type A and Type B Monoamine Oxidase Activity in Rat Brain Synaptosomes

Purpose

To determine the selective inhibition of the two forms of monoamine oxidase (MAO).

Introduction

The metabolic deamination of amines has been known for over a hundred years, but more recently Johnston (1) described two forms of monoamine oxidase, which are called "type A" and "type B". The existence of the two forms is based on different substrate and inhibitor specificities. Serotonin (5HT) and norepinephrine (NE) are substrates for type A MAO, $\beta$-phenethylamine (PEA) and benzylamine are substrates for type B MAO, while dopamine (DA) and tyramine are substrates for both types. Clorgyline is a selective inhibitor of the type A enzyme, deprenyl and pargyline are selective inhibitors of the type B enzyme and tranylcypromine and iproniazid are nonselective inhibitors (2). It is recognized that MAO inhibitors have antidepressant properties.

Although various methods for measuring MAO activity are available, the described method involves the extraction of the radiolabeled deaminated metabolites of [$^3$H]-5HT or [$^{14}$C]-$\beta$-phenethylamine. This procedure allows MAO-A and MAO-B activities to be measured either simultaneously or individually (3).

Procedure

A. Reagents

1. Phosphate buffer (0.5M), pH 7.4:
   134.4 g NaH$_2$PO$_4$.7H$_2$O q.s. to 1 liter in distilled H$_2$O (A)
   17.3 g Na$_2$HPO$_4$ q.s. to 250 ml in distilled H$_2$O (B)
   Adjust pH of A to 7.4 by slowly adding B (volumes as needed)
   Dilute 1: 10 in distilled H$_2$O (0.05M PO$_4$ buffer, pH 7.4)
2. 0.25M Sucrose (PO$_4$ buffered):
   21.4 g sucrose, q.s. to 250 ml with 0.05M PO$_4$ buffer
3. Substrate for MAO-A:
   a. Serotonin creatine SO$_4$ (5HT) is obtained from Sigma Chemical Company. A 5 mM stock solution is made up in 0.01N HCl. This is used to dilute the specific activity of the [$^3$H]-5HT.
   b. [$^3$H]-5-Hydroxytryptamine binoxalate (20–30 Ci/mmol) is obtained from New England Nuclear.
   c. Add 12 $\mu$l of [$^3$H]-5HT to 2 ml of the 5 mM 5HT solution. (Final amine concentration in the assay is 200 $\mu$M: see below.)
4. Substrate for MAO-B
   a. $\beta$-phenethylamine (PEA) is obtained from Sigma Chemical Company. A 5 mM stock solution is made up in 0.01N HCl. This is used to dilute the specific activity of the [$^{14}$C]-PEA.
   b. $\beta$-[ethyl-1-$^{14}$C]-phenethylaminehydrochloride(40–50 mCi/mmol) is obtained from New England Nuclear.
   c. Add 12 $\mu$l of [$^{14}$C]-PEA to 2 ml of the 5 mM PEA solution. (Final amine concentration in the assay is 200 $\mu$M: see below.)
5. Equal amounts of MAO-A (5HT) and MAO-B (PEA) substrates are combined for simultaneously testing both MAO types, i.e. mixed stock solution of 2.5 mM 5HT and 2.5 mM PEA, 40 $\mu$l of this mixed solution gives a 200 $\mu$M final concentration of each amine in the assay. When testing only one MAO type, the individual 5 mM stock solutions must be diluted 1: 1 with distilled water prior to adding 40 $\mu$l to the incubation mixture; i.e., same 200 $\mu$M final amine concentration.

B. Tissue Preparation

Male Wistar rats weighting 15–250 grams were sacrificed an removed. Whole brain minus cerebellum was homogenized in 30 volumes of ice-cold, phosphate-buffered 0.25M sucrose, using a Potter-Elvejhem homogenizer. The homogenate as centrifuged at 1000 g for 10 minutes and the supernatant (S$_1$) decanted and recentifuged at 18,000 g for 20 minutes. The resulting pellet (P$_2$) was resuspended in fresh 0.25M sucrose and served as the tissue source for mitochondrial MAO.

C. Assay

10 μl 0.5M PO₄ buffer, pH 7.4
50 μl H₂O or appropriate drug concentration
400 μl Tissue suspension Tubes are preincubated for 15 minutes at 37° C. and the assay is started by adding 40 μl of combined substrate ([$^3$H]-5HT and [$^{14}$C]-PEA) at 15 second intervals. The tubes are incubated for 30 minutes at 37° C. and the reaction stopped by the addition of 0.3 ml 2N HCl. Tissue blank values are determined by adding the acid before the radioactive substrate. The oxidative products of the reaction are extracted with ethyl acetate/toluene (1: 1). 5 ml of this mixture is added to the tubes, The resultant mixture is vortexed for 15 seconds to extract the deaminated metabolites into the organic phase and the latter is allowed to separate from the aqueous phase. The tubes are placed in acetone/dry ice bath to freeze the aquous layer. When this layer is frozen, the top organic layer is poured into a scintillation vial. 10 ml of Liquiscint is added and the samples are counted using window settings for in $^{14}$C in one channel and $^3$H in the second channel. IC$_{50}$ values are determined by log-probit analysis.

References

1. Johnston, J. P.: Some observations upon a new inhibitor of monoamine oxidase in brain tissue. Biochem. Pharmacol. 17: 1285-1297 (1968).
2. Fowler, C. J. and Ross, S. B.: Selective inhibitors of monoamine oxidase A and B: biochemical, pharmacological and clinical properties. Med. Res. Rev. 4: 323-328 (1984).
3. Kindt, M. V., Youngster, S. K., Sonsalla, P. K., Duvoisin, R. C. and Heikkila, R. E.: Role of monoamine oxidase-A (MAO-A) in the bioactivation and nigrostriatal dopaminergic neurotoxicity of the MPTP analog, 2'Me-MPTP. Eur. J. Pharmacol. 46: 313:-318 (1988).

Results of the monoamine oxidase inhibition assay for representative compounds of this invention are presented in Table 3.

TABLE 3

| Compound | Inhibitory Concentration - IC$_{50}$ (μM) | |
|---|---|---|
| | MAO-A | MAO-B |
| 1,2,3,4-Tetrahydro-cyclopent[b]indol-3-(2-propynyl)amine | 0.29 | 0.32 |
| 3-(N-cyclopropyl)amino-4-methyl-1,2,3,4-tetrahydrocyclopent[b]-indol-7-yl methylcarbamate | 0.32 | 0.42 |
| 4-Methyl-3-[(2-phenyl-cyclopropyl)imino]-1,2,3,4-tetrahydrocyclopent[b]indol-7-yl methylcarbamate | 15.2 | 3.7 |
| (Reference Compounds) | | |
| Deprenyl | 0.14 | 0.016 |
| Tranylcypromine | 0.19 | 0.12 |

The present inventors have also conducted Clonidine Binding Assay described below in order to ascertain the interaction of the compounds of this invention with α$_2$-receptors.

$^3$H-Clonidine Binding: α$_2$-Receptor

Introduction

A number of antidepressants have been shown to enhance neuronal release of norepinephrine by a presumed presynaptic α$_2$-receptor blockade and this property may be of significance with respect to the mechanism of action of these compounds. See references 1, 2 and 3 cited below. The interaction of a compound with central α$_2$-receptors is assessed in the $^3$H-clonidine binding assay.

Procedure

A. Reagents 1.
  a. 57.2 g Tris HCl, 16.2 g Tris Base—q.s. to 1 liter (0.5M Tris buffer, pH 7.7)
  b. Make a 1:10 dilution in distilled H$_2$O (0.05M Tris buffer, pH 7.7)
2. Tris buffer containing physiological ions
  a. Stock Buffer
     NaCl—7.014 g
     KCl—0.372 g
     CaC$_2$—0.222 g—q.s. to 100 ml in 0.5M Tris buffer
     MgCl$_2$—0.204 g
  b. Dilute 1:10 in distilled H$_2$O. This yields 0.05M Tris HCl, pH 7.7; containing NaCl (120 mM), KCl (5 mM), CaCl$_2$ (2 mM) and MgCl$_2$ (1 Mm)
3. [4-$^3$H]-Clonidine hydrochloride (20-30 Ci/mmol) is obtained from New England Nuclear. For IC$_{50}$ determinations: $^3$H-Clonidine is made up to a concentration of 120 nM and 50 μl added to each tube (yields a final concentration of 3 nM in the 2 ml volume assay).
4. Clonidine-HCl is obtained from Boehringer Ingelheim. A stock solution of 0.1 mM clonidine is made up to determine nonspecific binding. This yields a final concentration of 1 μM in the assay (20 μl to 2 ml).
5. Test compounds. For most assays, a 1 mM stock solution is made up in a suitable solvent and serially diluted, such that the final concentration in the assay ranges from 10$^{-5}$ to 10$^{-8}$M. Seven concentrations are used for each assay and higher or lower concentrations may be used, depending on the potency of the drug.

B. Tissue Preparation

Male Wistar rats are sacrificed by decapitation and the cortical tissue rapidly dissected. The tissue is homogenized in 50 volumes of 0.05M Tris buffer, pH 7.7 (buffer 1b) with the Brinkman Polytron, then centrifuged at 40,000 g for 15 minutes. The supernatant is discarded and the pellet re-homogenized in the original volume of 0.05M Tris buffer, pH 7.7 and re-centrifuged as before. The supernate is discarded and the final pellet re-homogenized in 50 volumes of buffer 2b. This tissue suspension is then stored on ice. The final tissue concentration is mg/ml. Specific binding is 1% of the total added ligand and 80% of total bound ligand.

Assay

100 μl—0.5M Tris-physiological salts, pH 7.7 (buffer 2a)
830 μl—H$_2$O
20 μl—Vehicle (for total binding) or 0. 1 mM clonidine (for nonspecific binding) or appropriate drug concentration
50 μl—$^3$H-clonidine stock
1000 μl tissue suspension Tissue homogenates are incubated for 20 minutes at 250° C. with 3 nM 3 H-clonidine and varying drug concentrations, and thereafter immediately filtered under reduced pressure on Whatman GF/B filters. The filters are washed with three five ml volumes of ice-cold 0.05M Tris buffer, pH 7.7, and thereafter transferred to scintillation vials. Ten ml of Liquiscint counting solution is added to each sample which is then counted by liquid scintillation spectroscopy. Specific clonidine binding is defined as the difference between total bound and that performed using log-probit analysis. The percent inhibition at each drug concentration is the mean of triplicate determinations.

References

1. P. F. Von Voigtlander, "Antidepressant and Antipsychotic Agents", in "Reports Medicinal Chemistry", F. H. Clarke, ed., Chapter 1, Academic Press, New York, N.Y.(1976);
2. S. Clements—Jewery, Neuropharmacol., 17, 779 (1978);
3. C. B. Smith and P. J. Hollingsworth, "Adrenergic Receptors and the Mechanism of Action of Antidepressant Treatments" in "Biochemical and Pharmacological Aspects of Depression", K. F. Tipton and M. B. H. Youdim, eds., Taylor and Francis, New York, N.Y., Chapter 4 (1989).

Results of the 3H-Clonidine Binding Assay for representative compounds of this invention are presented in Table 4.

TABLE 4

| $^3$H-Clonidine Binding | |
|---|---|
| Compound | IC$_{50}$ ($\mu$M) |
| 1,2,3,3a,4,8b-Hexahydro-cyclopent[b]indol-3-amine 2-naphthalenesulfonate hemihydrate | 1.27 |
| 4-Methyl-1,2,3,4-tetrahydro-cyclopent[b]indol-3-amine | 1.49 |
| 4-Methyl-3-phenylmethylimino-1,2,3,4-tetrahydrocyclopent-[b]indol-7-ol (Reference Compound) | 0.85 |
| Amitriptyline | 3.9 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric 2-naphthalenesulfonic and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
1,2,3,4-tetrahydrocyclopent[b]indol-3-amine;
4-methyl-1,2,3,4-tetrahydrocyclopent[b]indol-3-amine;
1,2,3,4-tetrahydrocyclopent[b]indol-3-cyclopropylamine;
-methyl-1,2,3,4-tetrahydrocyclopent[b]indol-3-cyclopropylamine;
1,2,3,4-tetrahydrocyclopent[b]indol-3-(2-propynyl)amine;
1,2,3,4-tetrahydrocyclopent[b]indol-3-(N-formyl)amine;
1,2,3,4-tetrahydrocyclopent[b]indol-3-(N-phenylmethoxycarbonyl)amine;
1,2,3,3a,4,8b-hexahydrocyclopent[b]indol-3-amine;

1,2,3,3a,4,8b-hexahydro-4-methylcyclopent[b]indol-3-amine;

1,2,3,3a,4,8b-hexahydro-4-methylcyclopent[b]indol-3-(2-propynyl)amine;

4-methyl-3-phenylmethylamino-1,2,3,4-tetrahydrocyclopent[b]indol-7-ol;

4-methyl-3-phenylmethylamino-1,2,3,4-tetrahydrocyclopent[b]indol-7-yl methylcarbamate;

3-(N-cyclopropyl)amino-4-methyl-1,2,3,4-tetrahydrocyclopent[b]-indol-7-ol;

3-(N-cyclopropyl)amino-4-methyl-1,2,3,4-tetrahydrocyclopent-[b]indol-7-yl methylcarbamate;

3-(N-cyclopropyl)amino-1,2,3,3a,4,8b-hexahydro-4-methylcyclopent[b]indol-7-ol;

3-(N-cyclopropyl)amino-1,2,3,3a,4,8b-hexahydrocyclopent[b]indol-7-yl phenylmethylcarbonate;

3-(N-cyclopropyl-N-methylaminocarbonyl)amino-1,2,3,3a,4,8b-hexahydrocyclopent[b]indol-7-yl phenylmethylcarbonate;

3-(N-cyclopropyl-N-methylaminocarbonyl)amino-1,2,3,3a,4,8b-hexahydro-4-methylcyclopent[b]indol-7-ol;

3-(N-cyclopropyl)amino-4-methyl-1,2,3,4-tetrahydrocyclopent[b]-indol-7-yl methylcarbamate;

1,2,3,3a,4,8b-hexahydro-4-methyl-3-phenylmethylaminocyclopent[b]indol-7-ol;

1,2,3,3a,4,8b-hexahydro-4-methyl-3-aminocyclopent[-b]indol-7-ol;

1,2,3,3a,4,8b-hexahydro-4-methyl-3-phenylmethoxycarbonylaminocyclopent[b]indol-7-ol;

1,2,3,3a,4,8b-hexahydro-4-methyl-3-(N-phenylmethoxycarbonyl)aminocyclopent[b]indol-7-yl methylcarbamate;

1,2,3,3a,4,8b-hexahydro-4-methyl-3-methylaminocarbonylaminocyclopent[b]indol-7-ol;

1,2,3,3a,4,8b-hexahydro-4-methyl-3-(N-phenylmethyl-N-methylaminocarbonyl)aminocyclopent[b]indol-7-ol;

4-t-butyloxycarbonyl-1,4-dihydrocyclopent[b]indol-3(2H)-one;

7-chloroacetyl-1,4-dihydro-4-methylcyclopent[b]indol-3(2H)-one;

7-chloroacetyloxy-1,4-dihydro-4-methylcyclopent[b]indol-3(2H)-one;

1,4-dihydro-7-hydroxy-4-methylcyclopent[b]indol-3(2H)-one;

1,4-dihydro-7-methylaminocarbonyloxy-4-methylcyclopent[b]indol-3(2H)-one;

3-hydroxyimino-7-methoxy-1,2,3,4-tetrahydrocyclopent[b]indole;

3-hydroxyimino-1,2,3,4-tetrahydrocyclopent[b]indole;

3-hydroxyimino-4-methyl-1,2,3,4-tetrahydrocyclopent[b]indole;

3-(2-aminoethyl)oximino-4-methyl-1,2,3,4-tetrahydrocyclopent[b]indole;

3-cyclopropylimino-1,2,3,4-tetrahydrocyclopent[b]indole;

3-cyclopropylimino-4-methyl-1,2,3,4-tetrahydrocyclopent[b]indole;

3-hydroxyimino-4-methyl-1,2,3,4-tetrahydrocyclopent[b]indol-7-ol;

3-acetyloxyimino-4-methyl-1,2,3,4-tetrahydrocyclopent[b]indol-7-yl acetate;

4-methyl-3-phenylmethylimino-1,2,3,4-tetrahydrocyclopent[b]indol-7-ol;

4-methyl-3-phenylmethylimino-1,2,3,4-tetrahydrocyclopent[b]indol-7-yl methylcarbamate;

4-methyl-3-[(2-phenylcyclopropyl)imino]-1,2,3,4-tetrahydrocyclopent-[b]indol-7-ol;

4-methyl-3-[(2-phenylcyclopropyl)imino]-1,2,3,4-tetrahydrocyclopent-[b]indol-7-yl methylcarbamate;

3-cyclopropylimino-4-methyl-1,2,3,4-tetrahydrocyclopent[b]indol-7-ol;

3-methylaminocarbonyloximino-4-methyl-1,2,3,4-tetrahydrocyclopent[b]indol-7-yl methylcarbamate;

3-(N-cyclopropyl)amino-1,2,3,3a,4,8b-hexahydro-4-methylcyclopent[b]-indol-7-yl methylcarbamate;

3-amino-1,2,3,3a,4,8b-hexahydro-4-methylcyclopent[-b]indol-7-yl 1,2,3,4-tetrahydroisoquinolylcarbamate;

5-bromo-3-(N-cyclopentyl)amino-1,2,3,3a,4,8b-hexahydro-4-methylcyclopent[b]indol-7-yl phenylmethylcarbamate;

3-[2-morpholinoethylamino]-4-methyl-1,2,3,4-tetrahydrocyclopent[b]-indol-7-yl phenylethylcarbamate; and 4-methyl-3-(4-piperidinyl)amino-1,2,3,4-tetrahydrocyclopent[b]indol-7-yl phenylethylcarbamate.

EXAMPLE 1

3-Hydroxyimino-7-methoxy-1,2,3,4-tetrahydrocyclopent b]indole

A stirred solution of 1,2-cyclopentadione mono-4-methoxyphenylhydrazone (6.0 g) in 100 ml of 10% aqueous $H_2SO_4$ was heated on a steam bath for 4 hours and thereafter allowed to cool to room temperature and filtered to give 1,4-dihydro 7-methoxycyclopent[b]indol-3(2H)-one as a solid. To the indole (2.6 g) in 25 ml of 95% EtOH was added hydroxylamine hydrochloride (1.7 g) in 15 ml water followed by sodium acetate (2.1 g) in 15 ml water. The mixture was heated at reflux for 2.5 hours and allowed to stand overnight. The EtOH was removed in vacuo and the solid i material which formed was collected and purified by flash chromatography to give 0.8 g of a mixture of oxime isomers.

| ANALYSIS: | | | |
|---|---|---|---|
| Calculated for $C_{12}H_{12}N_2O_2$: | 66.65% C | 5.59% H | 12.95% N |
| Found: | 66.39% C | 5.51% H | 12.91% N |

EXAMPLE 2

3-Hydroxyimino-1,2,3,4-tetrahydrocyclopent[b]indole

To a stirred solution of 1,4-dihydrocyclopent[b]indol-3(2H)-one* (10 g) in 100 ml of 95% EtOH was added hydroxylamine hydrochloride (8.3 g) in 20 ml water followed by sodium acetate (9.7 g) in 20 ml water. The mixture was heated at reflux for 2 hours and thereafter allowed to stand at room temperature overnight. The EtOH was removed in vacuo and the solid material which formed was collected and recrystallized from 95% EtOH to give 4.5 g of predominantly one oxime isomer in the first crop and 3.0 g of a mixture of oxime isomers from the second crop. A 1.5 g sample of the single isomer was recrystallized to provide 0.9 g of analytically pure material.

| ANALYSIS: | | | |
|---|---|---|---|
| Calculated for $C_{11}H_{10}N_2O$: | 70.95% C | 5.41% H | 15.04% N |
| Found: | 70.71% C | 5.32% H | 14.94% N |

EXAMPLE 3

3-Hydroxyimino-4-methyl-1,2,3,4-tetrahydrocyclopent[b]indole

To a stirred solution of 1,4-dihydro-4-methylcyclopent[b]indol-3(2H)-one (3.0 g) in 30 ml of 95% EtOH was added hydroxylamine hydrochloride (2.25 g) in 9 ml water followed by sodium acetate (4.4 g) in 9 ml water. The mixture was heated at reflux for 4 hours and thereafter an additional 1.1 gram of hydroxylamine hydrochloride in 5 ml water and 2.2 grams of sodium acetate in 5 ml i water were added. After an additional 2 hours of reflux, the mixture was allowed to stand at room temperature overnight. The material which precipitated was collected and recrystallized from 95% EtOH to give 1.9 grams of analytically pure material.

| ANALYSIS: | | | |
| --- | --- | --- | --- |
| Calculated for $C_{12}H_{12}N_2O$: | 71.98% C | 6.04% H | 13.99% N |
| Found: | 72.18% C | 6.11% H | 14.00% N |

EXAMPLE 4

3-(2-Aminoethyl)oximino-4-methyl-1,2,3,4-tetrahydrocyclopent[b]indole

To a stirred suspension of 3-hydroxyimino-4-methyl-1,2,3,4-tetrahydrocyclopent[b]indole (5.0 g) in methylene chloride (50 ml) was added 50% NaOH (50 ml) followed by tetrabutylammonium bromide (800 mg) and bromoethylamine hydrobromide (7.6 g). The reaction mixture was stirred overnight at room temperature. The layers were separated and the aqueous layer was extracted with methylene chloride (50 ml). The organic layers were combined, dried ($Na_2SO_4$) and concentrated. The product was purified via flash chromatography on silica gel eluting with 10% methanol/methylene chloride to provide 1.1 grams of purified material.

EXAMPLE 5

1,2,3,4-Tetrahydrocyclopent[b]indol-3-amine

To a stirred solution of 3-hydroxyimino-1,2,3,4-tetrahydrocyclopent[b]indole (6 g) in 150 ml of 95% EtOH at 0° C. was added a nickel alloy (Harshaw, Ni-100P, 10 g) followed by 12.9 grams of sodium hydroxide in 150 ml water. The ice bath was removed after 0.5 hour and the mixture was stirred an additional hour and filtered. The EtOH was removed in vacuo and the product crystallized to provide 5.0 grams of solid. A sample was recrystallized from toluene to provide analytically pure material.

| ANALYSIS: | | | |
| --- | --- | --- | --- |
| Calculated for $C_{11}H_{12}N_2$: | 76.71% C | 7.02% H | 16.26% N |
| Found: | 76.44% C | 6.98% H | 15.99% N |

EXAMPLE 6

4-Methyl-1,2,3,4tetrahydrocyclopent[b]indol-3-amine hydrochloride

To a stirred solution of 3-hydroxyimino-4-methyl-1,2,3,4-tetrahydrocyclopent[b]indole (5 g) in 200 ml 95% EtOH at 0° C. was added a nickel alloy (9 g) followed by 11 grams of sodium hydroxide in 200 ml water. The ice bath was removed after 0.25 hours and the mixture was stirred an additional hour. Additional nickel alloy (2×1 gram) was added and the mixture was stirred for 2 hours. The catalyst was removed by filtration, the EtOH was removed in vacuo and the product extracted into $CH_2Cl_2$ (2×100 ml). The $CH_2Cl_2$ extracts were dried ($Na_2SO_4$) and concentrated to give an oil (4.5 g). The oil (2.0 g) was dissolved in diethyl ether (100 ml) and ethereal HCl was added until the solution became slightly acidic. The solid which formed was filtered and dried overnight to provide 1.6 grams of 4-methyl-1,2,3,4-tetrahydrocyclopent[b]indole-3-amine hydrochloride.

| ANALYSIS: | | | |
| --- | --- | --- | --- |
| Calculated for $C_{12}H_{14}N_2.HCl$: | 64.72% C | 6.79% H | 12.58% N |
| Found: | 64.41% C | 6.82% H | 12.18% N |

EXAMPLE 7

4-t-Butyloxycarbonyl-1,4-dihydrocyclopent[b]indol-3(2H)-one

To a stirred solution of 1,4-dihydrocyclopent[b]indol-3(2H)-one (10.0 g) in acetonitrile (100 ml) was added di-t-butylpyrocarbonate (15 g), followed by 4-dimethylaminopyridine (700 mg). The mixture was stirred overnight at room temperature under nitrogen. The solvent was removed under reduced pressure and the residue was purified by flash column chromatography to provide 4-t-butyloxycarbonyl-1,4-dihydrocyclopent[b]indole-3(2H)-one (4.5 g) as a solid.

| ANALYSIS: | | | |
| --- | --- | --- | --- |
| Calculated for $C_{16}H_{17}NO_3$: | 70.83% N | 6.32% H | 5.16% N |
| Found: | 71.04% C | 6.35% H | 5.16% N |

EXAMPLE 8

1,2,3,4-tetrahydrocyclopent[b]indol-3-cyclopropylamine hydrochloride 1,4-dihydrocyclopent[b]indol-3(2H)-one (5.0 g) was separated into two portions and placed into sealed tubes each containing toluene (20 ml), cyclopropylamine (2.0 ml) and 3 A molecular sieves (1 g). The mixtures were placed in an oil bath and refluxed for 7 hours. Each tube was allowed to cool to ambient temperature, the molecular sieves were filtered, and the filtrate concentrated to give a brown solid which was identified as the imine via NMR/MS. The combined imine product was dissolved in isopropanol (125 ml) and methanol (25 ml), and thereafter sodium borohydride (2.66 g) was added and the mixture was stirred under nitrogen at ambient temperature overnight. The mixture was cooled to 0° C., water was slowly added and the mixture was stirred 0.5 hours. The mixture was extracted with EtOAc (2×200 ml), the EtOAc layer was extracted with 10% HCl (2×200 ml) and the acid extracts were neutralized (10% NaOH) and extracted with EtOAc (3×200 ml). The EtOAc extracts were dried ($Na_2SO_4$) and concentrated in vacuo to give 3.5 grams of product. A 1.5 gram sample was dissolved in $Et_2O$ (100 ml) and ethereal HCl was added, the precipitate was collected and dried to provide 1,2,3,4-tetrahydrocyclopent[b]indol-3-cyclopropylamine hydrochloride.

| ANALYSIS: | | | |
|---|---|---|---|
| Calculated for $C_{14}H_{16}N_2 \cdot HCl$: | 67.60% C | 6.89% H | 11.26% N |
| Found: | 67.22% C | 6.87% H | 10.79% N |

EXAMPLE 9

4-Methyl-1,2,3,4-tetrahydrocyclopent[b]indol-3-cyclopropylamine-2-naphthalene sulfonate 1,4-Dihydro-4-methylcyclopent[b]indol-3(2H)-one (2.0 g) and cyclopropylamine (3.0 g) were dissolved in 30 ml toluene and cooled to $-100°$ C. Titanium tetrachloride (0.70 ml) was dissolved in 10 ml toluene and added to the first solution. The reaction mixture was allowed to warm to room temperature and stirred overnight. The imine was isolated by filtering the mixture through a pad of silica and removing the solvent in vacuo. The imine (2.4 g) was dissolved in 100 ml of 5:1 iPrOH/MeOH and thereafter sodium borohydride (1.2 g) was added. The reaction mixture was stirred overnight. The solvents were removed and the product purified by chromatography isolating the product as a yellow oil (1.6 g).

A 0.75 g portion of the cyclopropylaminoindole compound was dissolved in 75 ml $Et_2O$ and stirred while a solution of 0.69 g of 2-naphthalene sulfonic acid in 50 ml $Et_2O$ was added slowly. A white precipitate formed which was filtered under $N_2$, washed with $2 \times 50$ ml $Et_2O$ and dried to afford 1.04 g of 4-methyl-1,2,3,4-tetrahydrocyclopent[b]indol-3-cyclopropylamine 2-naphthalene sulfonate.

| ANALYSIS: | | | |
|---|---|---|---|
| Calculated for $C_{15}H_{18}N_2 \cdot C_{10}H_8SO_3$: | 69.10% C | 6.03% H | 6.45% N |
| Found: | 68.98% C | 6.04% H | 6.39% N |

EXAMPLE 10

1,2,3,4-Tetrahydrocyclopent[b]indol-3-(2-propynyl)amine

To a stirred solution of 1,2,3,4-tetrahydrocyclopent[b]indol-3-amine (5.0 g) in tetrahydrofuran (30 ml) under nitrogen was added triethylamine (2.9 g) followed by a dropwise addition of propargyl bromide (4.45 g, 80% solution in toluene) dissolved in tetrahydrofuran (20 ml). The mixture was stirred overnight. Additional propargyl bromide (0.01 mole) dissolved in tetrahydrofuran (10 ml) was added and the mixture was stirred for 3 hours. The mixture was concentrated in vacuo, $CH_2Cl_2$ (150 ml) was added and the mixture was extracted with 10% HCl ($2 \times 50$ ml). The organic phase was dried ($Na_2SO_4$) and concentrated to give 0.85 gram of product. The reaction was repeated on the same scale using identical conditions. The products were combined and chromatographed on silica gel eluting with 5% $MeOH/CH_2Cl_2$ to provide 1,2,3,4-tetrahydrocyclopent[b]indol-3-(2-propynyl)amine (1.6 g).

| ANALYSIS: | | | |
|---|---|---|---|
| Calculated for $C_{14}H_{14}N_2$: | 79.97% C | 6.71% H | 13.32% N |
| Found: | 79.70% C | 6.77% H | 13.14% N |

EXAMPLE 11

1,2,3,4-Tetrahydrocyclopent[b]indol-3-(N-formyl)amine

To a stirred solution of 1,2,3,4-tetrahydrocyclopent[b]indol-3-amine (2.0 g) in 25 ml methylene chloride at room temperature was added 4-dimethylaminopyridine (1.4 g) followed by 0.46 ml of formic acid. 1-(3-Dimethylaminopropyl)-3-ethylcarbodiimide hydrochloride (2.24 g) was added and the mixture was stirred overnight under a nitrogen atmosphere. The reaction mixture was diluted with $CH_2Cl_2$ (100 ml), extracted with water ($3 \times 50$ ml), dried ($Na_2SO_4$) and concentrated in vacuo to give a solid which was crystallized from EtOH and recrystallized from toluene to provide 1,2,3,4-tetrahydrocyclopent[b]indol-3-(N-formyl)amine (1.1 g).

| ANALYSIS: | | | |
|---|---|---|---|
| Calculated for $C_{12}H_{12}N_2O$: | 71.98% C | 6.04% H | 13.99% N |
| Found: | 71.91% C | 5.86% H | 13.54% N |

EXAMPLE 12

1,2,3,4-Tetrahydrocyclcopent[b]indol-3-(N-phenylmethoxycarbonyl)amine

To a stirred solution of 1,2,3,4-tetrahydrocyclopent[b]indol-3-amine (5 g) in 50 ml $CH_2Cl_2$ at room temperature was added triethylamine (3.2 g) followed by 5.4 grams of benzyl chloroformate in 25 ml $CH_2Cl_2$. The mixture was stirred for 2 hours and thereafter washed successively with water (50 ml), 10% HCl (50 ml) and water (50 ml). The $CH_2Cl_2$ solution was dried ($Na_2SO_4$), concentrated in vacuo and purified by flash chromatography eluting with 2:1 hexane/acetone to give 2.0 grams 1,2,3,4-tetrahydrocyclopent[b]indol-3-(N-phenylmethoxycarbonyl)amine.

| ANALYSIS: | | | |
|---|---|---|---|
| Calculated for $C_{19}H_{18}N_2O_2$: | 74.49% C | 5.92% H | 9.14% N |
| Found: | 74.23% C | 5.99% H | 8.96% N |

EXAMPLE 13

1,2,3,3a,4,8b-Hexahydrocyclopent[b]indol-3-amine 2-naphthalene sulfonate hemihydrate 1,2,3,4-Tetrahydrocyclopent[b]indol-3-amine (2.0 g) was placed in a three-neck flask under nitrogen and 34 ml of a 1.0M borane-tetrahydrofuran complex in tetrahydrofuran was added dropwise via a syringe. The mixture was stirred at 0° C. for 0.5 hour and thereafter trifluroacetic acid (34 ml) was added in a dropwise manner. After stirring for 2 hours, the tetrahydrofuran was removed in vacuo, and the residue was made basic with 10% NaOH, extracted with $CH_2Cl_2$ ($2 \times 75$ ml) and concentrated to an oil (2 grams). A 1.0 gram sample of the oil was dissolved in ether (200 ml) and a solution of 1.3 grams of 2-napthalene sulfonic acid in ether was added in a dropwise manner with stirring. The precipitate which formed was collected by filtration under nitrogen.

| ANALYSIS: | | | |
|---|---|---|---|
| Calculated for $C_{11}H_{15}N_2$·$C_{10}H_8SO_3$·$0.5H_2O$: | 64.41% C | 5.93% H | 7.15% N |
| Found: | 64.34% C | 5.33% H | 6.73% N |

EXAMPLE 14

1,2,3,3a,4,8b-Hexahydro-4-methylcyclopent[b]indol-3-amine 2-naphthalene sulfonate 4-Methyl-1,2,3,4-tetrahydrocyclopent[b]indol-3-amine (10.2 g) was placed in a three-neck flask under nitrogen and 17 ml of a 1.0M borane-tetrahydrofuran complex in tetrahydrofuran was added dropwise via a syringe. The mixture was stirred at 0° C. for 0.5 hours and thereafter trifluoroacetic acid (1 85 ml) was added via a pressure-addition funnel. After stirring for 1 hour, the tetrahydrofuran was removed in vacuo, and the residue was basified with 10% NaOH (PH=8), extracted with $CH_2Cl_2$ (2×500 ml), dried over $Na_2SO_4$ and concentrated to an oil (10.3 g). The crude material was purified by column chromatography.

A 1.7 g sample of 1,2,3,3a,4,8b-hexahydro-4-methylcyclopent[b]indol-3-amine was dissolved in 150 ml $Et_2O$ and a solution of 1.9 g of 2-naphthalene sulfonic acid in ether was added in a dropwise manner with stirring. A solid was collected by filtration under $N_2$.

| ANALYSIS: | | | |
|---|---|---|---|
| Calculated for $C_{12}H_{17}N_2$·$C_{10}H_8SO_3$: | 66.64% C | 6.10% H | 7.06% N |
| Found: | 66.74% C | 5.66% H | 6.77% N |

EXAMPLE 15

1,2,3,3a,4,8b-hexahydro-4-methylcyclopent[b]indol-3-(2-propynyl)amine hydrochloride 1,2,3,3a,4,8b-Hexahydro-4-methylcyclopent[b]indol-3-amine (5.0 grams) was dissolved in 50 ml tetrahydrofuran along with triethylamine (2.7 grams). The solution was cooled to 0° C. and propargyl bromide (3.2 grams) in 20 ml tetrahydrofuran was added slowly. After the addition, the mixture was allowed to come up to room temperature and stirred overnight. The tetrahydrofuran was stripped off and the residue taken up in 200 ml $CH_2Cl_2$. The organic layer was extracted with 10% HCl (2×70 ml). The aqueous fractions were combined and basified with 10% NaOH. The aqueous layer was extracted with 2×200 ml $CH_2Cl_2$ and the organic layers were combined and dried over sodium sulfate. The solvent was removed in vacuo. Flash chromatography on silica gel gave 1,2,3,3a,4,8b-hexahydro-4-methylcyclopent[b]indol-3-(2-propynyl)amine (2.0 grams) as a reddish brown oil.

A 1.46 g sample of the indoline was dissolved in ether and stirred vigorously. An ethereal HCl solution was added to this solution until neutral (pH=6). The solids were then filtered and dried under $N_2$ giving 1,2,3,3a,4,8b-hexahydro-4-methylcyclopent[b]indol-3-(2-propynyl)amine hydrochloride as a fine white powder (1.46 grams).

| ANALYSIS: | | | |
|---|---|---|---|
| Calculated for $C_{15}H_{18}N_2$·HCl: | 68.56% C | 7.30% H | 10.68% N |
| Found: | 68.21% C | 7.27% H | 10.54% N |

EXAMPLE 16

7-Chloroacetyl-1,4-dihydro-4-methylcyclopent[b]indol-3(2H)-one

Aluminum chloride (8.5g) was suspended in $CH_2Cl_2$ (20 ml) at 0° C., chloroacetyl chloride (7.2 g) was slowly added and the mixture was stirred for 5 minutes. This mixture was added dropwise to a stirred solution of 1,4-dihydro-4-methylcyclopent[b]indol-3(2H)-one (6.0 g) in 100 ml $CH_2Cl_2$ at 0° C. The mixture was stirred at 0° C. for 45 minutes and thereafter an additional equivalent of preformed solution of aluminum chloride and chloroacetyl chloride in methylene chloride was introduced in a dropwise manner. After 30 minutes the reaction mixture was slowly poured into a stirred ice/water mixture. The layers were separated and the $CH_2Cl_2$ layer was washed with $NaHCO_3$, dried ($Na_2SO_4$) and concentrated to an oil. Purification by flash chromatography on silica gel eluting with hexane/acetone provided 7-chloroacetyl-1,4-dihydro-4-methylcyclopent[b]indol-3(2H)-one (4.5 g).

| ANALYSIS: | | | |
|---|---|---|---|
| Calculated for $C_{14}H_{12}ClNO_2$: | 64.25% C | 4.62% H | 5.35% N |
| Found: | 64.35% C | 4.61% H | 5.24% N |

EXAMPLE 17

7-Chloroacetyloxy-1,4-dihydro-4-methylcyclopent[b]indol-3(2H)-one

To a stirred solution of 7-chloroacetyl-1,4-dihydro-4-methylcyclopent-[b]indol-3(2H)-one (2.0 g) in chloroform (100 ml) was added sodium phosphate (1.02 g) followed by m-chloroperbenzoic acid (2.5 g, 50–60% purity). The mixture was stirred at room temperature under a nitrogen atmosphere for 14 hours. Saturated $NaHCO_3$ aqueous solution (50 ml) was added, the layers separated and the organic layer washed with water (2×50 ml). The solution was dried ($Na_2SO_4$), filtered and concentrated to give a yellow oil which crystallized upon standing. Recrystallization from with EtOH provided 7-chloroacetyloxy-1,4-dihydro-4-methylcyclopent[b]indol-3(2H)-one (1.1 g).

| ANALYSIS: | | | |
|---|---|---|---|
| Calculated for $C_{14}H_{12}ClNO_3$: | 60.55% C | 4.36% H | 5.04% N |
| Found: | 60.47% C | 4.33% H | 4.98% N |

EXAMPLE 18

1,4-Dihydro-7-methylaminocarbonyloxy-4-methylcyclopent-[b]indol-3(2H)-one

7-Chloroacetyloxy-1,4-dihydro-4-methylcyclopent[-b]indol- 3(2H)-one (5.0 g) was suspended in EtOH (100 ml), and thereafter 10% NaOH solution (50 ml) was added and the mixture was stirred at room temperature for 3 hours. The mixture was concentrated in vacuo, $CH_2Cl_2$ (100 ml) was added followed by 10% HCl until the aqueous layer was neutralized. The layers were separated and the aqueous phase extracted with CH$_2$Cl$_2$ (2×100 ml). The organic portion was dried (Na$_2$SO$_4$) and concentrated and the residue was recrystallized from 95% EtOH to provide 1,4-dihydro-7-hydroxy-4-methylcyclopent[b]indol-3(2H)-one as an off-white solid. The phenol was dissolved in CH$_2$Cl$_2$ (100 ml), and thereafter 1,8-diazabicyclo[5.4.0]undec-7-ene (0.4 g) was added followed by methyl isocyanate (1.4 g) and the mixture was stirred overnight. The mixture was concentrated in vacuo to afford an oily solid which was crystallized from EtOH to provide 1,4-dihydro-7-methylaminocarbonyloxy-4-methylcyclopent[b]indol-3(2H)-one (1.1 g).

| ANALYSIS: | | | |
|---|---|---|---|
| Calculated for C$_{14}$H$_{14}$N$_2$O$_3$: | 65.11% C | 5.46% H | 10.85% N |
| Found: | 65.20% C | 5.32% H | 10.74% N |

EXAMPLE 19

3-Acetyloxyimino-4-methyl-1,2,3,4-tetrahydrocyclopent[b]indol-7-yl acetate

7-Chloroacetyloxy-1,4-dihydro-4-methylcyclopent[b]indol-3(2H)-one (8.0 g) was suspended in EtOH (200 ml) and a solution of NaOAc (15.6 g) in water (25 ml) and a solution of hydroxylamine hydrochloride (8.0 g) in water (25 ml) were added and the mixture was refluxed for 3 hours. The mixture was concentrated in vacuo and the residue was recrystallized from 95% EtOH to provide 3-hydroxyimino-4-methyl-1,2,3,4-tetrahydrocyclopent[b]indol-7-ol as an off-white solid. The oxime was dissolved in tetrahydrofuran (100 ml), and thereafter acetic anhydride (8.1 g) and 4-dimethylaminopyridine (400 mg) were added and the mixture was stirred under nitrogen at ambient temperature overnight. The mixture was concentrated in vacuo, CH$_2$Cl$_2$ (100 ml) was added and the solution was washed successively with water (50 ml), 5% NaHCO$_3$ (50 ml) and water (50 ml). After drying (Na$_2$SO$_4$), the solvent was removed in vacuo and the product recrystallized from EtOH to provide 3-acetyloximino-4-methyl-1,2,3,4-tetrahydrocyclopent[b]indol-7-yl acetate (1.7 g).

| ANALYSIS: | | | |
|---|---|---|---|
| Calculated for C$_{16}$H$_{16}$N$_2$O$_2$: | 63.99% C | 5.37% H | 9.33% N |
| Found: | 63.56% C | 5.37% H | 9.29% N |

EXAMPLE 20

4-Methyl-3-phenylmethyl-tetrahydrocyclopent-[b]indol-7-ol

To a stirred suspension of 7-chloroacetyloxy-1,4-dihydro-4-methylcyclopent[b]-indol-3(2H)-one (6.0 g) in toluene (50 ml) was added benzylamine (9.2 g) and the mixture was heated at reflux temperature with azeotropic removal of water using a Dean Stark trap. After 4 hours, TLC analysis indicated complete conversion to product. The mixture was allowed to cool to room temperature and filtered, and the solid material was washed with acetonitrile. The filtrate and washings were combined, concentrated and purified by flash chromatography on silica gel (2:1 hexane/acetone as eluent). The crystals which formed in the product-containing fractions were collected via filtration to give 4-methyl-3-phenylmethylimino-1,2,3,4-tetrahydrocyclopent[b]indol-7-ol (1.1 grams) and the filtrate was concentrated to give an oil (3.0 grams) which crystallized upon standing.

| ANALYSIS: | | | |
|---|---|---|---|
| Calculated for C$_{19}$H$_{18}$N$_2$O: | 78.59% C | 6.25% H | 9.65% N |
| Found: | 78.62% C | 6.21% H | 9.63% N |

EXAMPLE 21

4-Methyl-3-phenylmethylamino-1,2,3,4-tetrahydrocyclopent[b]indol-7-ol

To a stirred solution prepared from 4-methyl-3-phenylmethylimino-1,2,3,4-tetrahydrocyclopent[b]indol-7-ol (16.0 g), isopropanol (200 ml) and methanol (50 ml) was added sodium borohydride (4.8 g) and the mixture was stirred under nitrogen at ambient temperature for 3 hours. The mixture was cooled to 0° C., water was slowly added and the mixture was stirred 0.5 hour. The mixture was extracted with CH$_2$Cl$_2$ (2×200 ml), and the CH$_2$Cl$_2$ extracts were dried (Na$_2$SO$_4$), Concentrated and chromatographed on silica gel eluting with 2:1 hexanes/acetone. The product-containing fractions were combined to give 4.25 grams of 4-methyl-3-(phenylmethylamino)-1,2,3,4-tetrahydrocyclopent[b]indol-7-ol.

| ANALYSIS: | | | |
|---|---|---|---|
| Calculated for C$_{19}$H$_{20}$N$_2$O: | 78.05% C | 6.89% H | 9.58% N |
| Found: | 78.20% C | 6.97% H | 9.54% N |

4-Methyl-3-phenylmethylimino-1,2,3,4-tetrahydrocyclopent[b]indol-7-yl methylcarbamate

EXAMPLE 22

To a stirred solution of 4-methyl-3-phenylmethylimino-1,2,3,4-tetrahydrocyclopent[b]indol-7-ol (2.0 g) in CH$_2$Cl$_2$ (40 n-A) was added 1,8-diazabicyclo[5.4.-0]undec-7-ene (0.16 g) followed by the dropwise addition of methyl isocyanate (0.39 g) in CH$_2$Cl$_2$ (10 ml). The reaction was monitored via TLC and after 3 hours the solution was concentrated and the precipitate was collected and recrystallized from acetonitrile to give 4-methyl-3-phenylmethylimino-1,2,3,4-tetrahydrocyclopent[b]indol-7-yl methylcarbamate (1.85 grams).

| ANALYSIS: | | | |
|---|---|---|---|
| Calculated for C$_{21}$H$_{21}$N$_3$O$_2$: | 72.60% C | 6.09% H | 12.09% N |
| Found: | 72.59% C | 6.01% H | 12.05% N |

EXAMPLE 23

4-Methyl-3-phenylmethylamino-1,2,3,4-tetrahydrocyclopent[b]indol-7-yl methylcarbamate maleate To a stirred solution of 4-methyl-3-phenylmethylimino-1,2,3,4-tetrahydrocyclopent[b]indol-7-yl methylcarbamate (1.8 g) in acetic acid (25 ml) was added sodium cyanoborohydride (0.8 g). The reaction was monitored via TLC and after 2 hours CH$_2$Cl$_2$ (50 ml) was added and the solution was washed with saturated NaHCO$_3$ until neutral. The CH$_2$Cl$_2$ layer was dried (Na$_2$SO$_4$), filtered and concentrated to give an oil which was purified via flash chromatography, eluting with 2:1 hexane/acetone. The product-containing fractions were collected and concentrated to an oil which was dissolved in ether and thereafter an ethereal maleic acid solution was added until the mixture became acidic. The maleate salt of 4-methyl-3-phenylmethylamino-1,2,3,4-tetrahydrocyclopent[b]indol-7-yl methylcarbamate (0.8 g) which precipitated as a colorless solid was collected.

| ANALYSIS: | | | |
|---|---|---|---|
| Calculated for $C_{21}H_{21}N_3O_2 \cdot C_4H_4O_4$: | 64.51% C | 5.85% H | 9.03% N |
| Found: | 64.13% | 5.75% H | 8.97% N |

EXAMPLE 24

4-Methyl-3-[(2-phenylcyclopropyl)imino]-1,2,3,4-tetrahydrocyclopent[b]indol-7-yl methylcarbamate To a stirred suspension of 1,4-dihydro-7-hydroxy-4-methylcyclopent[b]indol-3(2H)-one (5.0 g) in acetonitrile (100 ml) was added phenylcyclopropylamine hydrochloride (4.2 g) followed by triethylamine (2.5 g). The solution was stirred at room temperature under a nitrogen atmosphere while titanium (IV) isopropoxide was added in a dropwise manner. The mixture was stirred for 3 hours and thereafter quenched with ice/water. The mixture was filtered, the solids were washed with $CH_2Cl_2$, the layers were separated and the organic portion was dried ($Na_2SO_4$). After concentration, the crude product was purified via flash chromatography eluting with hexane/acetone (2: 1) to give 4-methyl-3-[(2-phenylcyclopropyl)imino]-1,2,3,4-tetrahydrocyclopent[b]indol-7-ol.

To a stirred solution of this product (1.0 g) in $CH_2Cl_2$ (9.0 ml) was added 1,8-diazabicyclo[5.4.0]undec-7-ene (68 mg) followed by the dropwise addition of methyl isocyanate (0.18g) in $CH_2Cl_2$(1.0 ml). The reaction was monitored via TLC and after 0.5 hour the solution was concentrated and the precipitate was collected and recrystallized twice from acetonitrile to give 4-methyl-3-[(2-phenylcyclopropyl)imino]-1,2,3,4-tetrahydrocyclopent[b]indol-7-yl methylcarbamate (0.55 gram).

| ANALYSIS: | | | |
|---|---|---|---|
| Calculated for $C_{21}H_{21}N_3O_2$: | 73.97% C | 6.21% H | 11.25% N |
| Found: | 73.57% C | 6.25% H | 11.13% N |

EXAMPLE 25

3-Cyclopropylimino-4-methyl-1,2,3,4-tetrahydrocyclopent-[b]indol-7-ol

7-Chloroacetyloxy-1,4-dihydro-4-methylcyclopent[b]indol-3(2H)-one (15.0 g) and cyclopropylamine (9.6 g) were dissolved in 300 ml toluene and cooled to $-100°$ C. Titanium tetrachloride (6.3 g) dissolved in 50 ml toluene was added slowly to the first solution. The reaction mixture was allowed to come up to room temperature and stirred overnight. The next day another 1.5 equivalents of the amine (4.6 g) was added to the reaction mixture and the mixture was stirred for one hour. The reaction mixture was filtered through a pad of silica gel, eluting with 3:1 hexane/ethyl acetate, giving a yellow oil after removal of solvents. 3-Cyclopropylimino-4-methyl-1,2,3,4-tetrahydrocyclopent[b]indol-7-ol was isolated as a light yellow solid (3.3 g) after flash chromatography and recrystallization from ethyl acetate.

| ANALYSIS: | | | |
|---|---|---|---|
| Calculated for $C_{15}H_{16}N_2O$: | 74.97% C | 6.71% H | 11.66% N |
| Found: | 74.57% C | 6.54% H | 11.37% N |

EXAMPLE 26

3-(N-Cyclopropyl)amino-4-methyl-1,2,3,4-tetrahydrocyclopent[b]indol-7-ol maleate 3-Cyclopropylimino-4-methyl-1,2,3,4-tetrahydrocyclopent[b]indol-7-ol (17.3 g) was dissolved in 5:1 isopropanol/methanol (250 ml), under $N_2$ and stirred at room temperature. Sodium borohydride (8.2 g) was added and the reaction mixture was stirred overnight. Thin layer analysis indicated a complete reaction. The solution was cooled to 0° C. and water (100 ml) was added slowly. Ethyl acetate (250 ml) was added and, after separating the layers, the organic portion was washed successively with brine (2×100 ml), and water (2×100 ml) and dried over $Na_2SO_4$, and thereafter the solvent was removed in vacuo. The crude material was purified by preparative HPLC using a 2:1 hexane/ethyl acetate solvent system. The free base was isolated as light brown/yellow oil (7.8 g). A stirred solution of the free base (0.6 g) in ether (200 ml) was treated slowly with a solution prepared from 0.3 g maleic acid, 50 ml $Et_2O$ and 5 ml EtOH. 3-(N-Cyclopropyl)amino-4-methyl-1,2,3,4-tetrahydrocyclopent[b]indol-7-ol maleate was isolated as a light yellow solid (0.8 g) after filtering and drying under $N_2$.

| ANALYSIS: | | | |
|---|---|---|---|
| Calculated for $C_{15}H_{18}N_2O$. | 63.68% C | 6.19% H | 7.82% N |
| Found: | 63.47% C | 6.31% H | 7.69% N |

EXAMPLE 27

3-(N-Cyclopropyl)amino-4-methyl-1,2,3,4-tetrahydrocyclopent[b]indol-7-yl phenylmethylcarbonate 3-(N-Cyclopropyl)amino-4-methyl-1,2,3,4-tetrahydrocyclopent[b]-indol-7-ol (5.5 g) was dissolved in 250 ml $CH_2Cl_2$ along with triethylamine (2.8 g) and cooled to 0° C. while stir-ring. Benzyl chloroformate (3.9 g) dissolved in 50 ml $CH_2Cl_2$ was added slowly to the first solution. After complete addition, the reaction mixture was allowed to come to room temperature, washed with $H_2O$ (2×150 ml) and dried over $Na_2SO_4$, and the solvent was removed in vacuo. The crude material was purified by flash column chromatography using EtOAc as the solvent. 3-(N-Cyclopropyl)amino-4-methyl-1,2,3,4-tetrahydrocyclopent[b]indol-7-yl phenylmethylcarbonate was isolated as a yellow brown foam (4.1 g).

| ANALYSIS: | | | |
|---|---|---|---|
| Calculated for $C_{23}H_{24}N_2O_3$: | 73.38% C | 6.43% H | 7.44% N |
| Found: | 73.41% C | 6.80% H | 7.48% N |

EXAMPLE 28

3-(N-Cyclopropyl)amino-1,2,3,3a,4,8b-hexahydro-4-methylcyclopent[b]indol-7-ol 3-Cyclopropylimino-4-methyl-1,2,3,4-tetrahydrocyclopent-[b]indol-7-ol (8.7 g) was placed in a 3-neck flask and cooled to 0° C. in an ice-water bath. A 1M solution of borane in THF (540 ml) was added in a dropwise manner. The mixture was stirred for 1 hour while it was slowly warmed to room temperature. The mixture was cooled back down to 0° C. and trifluoroacetic acid (119 ml) was added in a dropwise manner. The solution was stirred for 15 minutes and THF was removed in vacuo. The mixture was neutralized with 10% NaOH solution, extracted with methylene chloride (4×500 ml), dried (Na$_2$SO$_4$) and concentrated to give 3-(N-cyclopropyl)amino-1,2,3,3a,4,8b-hexahydro-4-methylcyclopent[b]indol-7-ol (8.8 g).

EXAMPLE 29

3-(N-Cyclopropyl-N-methylaminocarbonyl)amino-1,2,3,3a,4,8b-hexahydro-4-methylcyclopent[b]indol-7-ol hydrochloride 3-(N-Cyclopropyl)amino-1,2,3,3a,4,8b-hexahydro-4-methylcyclopent[b]indol-7-ol (8.8 g) was dissolved in CH$_2$Cl$_2$ (400 ml) along with triethylamine (4.4 g). The solution was cooled to 0° C. and stirred under N$_2$. Benzyl chloroformate (6.1 g) dissolved in CH$_2$Cl$_2$ (50 ml) was added slowly to the first solution. The reaction was monitored by thin layer chromatography while adding an additional equivalent (6.1 g) of the chloroformate until the reaction was complete. The solution was warmed to room temperature before washing with water (2×100 ml), drying over Na$_2$SO$_4$ and concentrating to an oil, which was purified by preparative HPLC using 3:1 hexane/acetone as the solvent system. 3-(N-Cyclopropyl)amino-1,2,3,3a,4,8b-hexahydro-4-methylcyclopent[b]indol-7-yl phenylmethylcarbonate was isolated (7.0 g), which was characterized by NMR, MS and IR. This material was dissolved in CH$_2$Cl$_2$ (250 ml) and the solution treated with 1,8-diazabicyclo[5.4.0]undec-7-ene (DBU; 0.4 g). The mixture was cooled to 0° C. and stirred while h solution of methyl isocyanate (1.1 g) in 50 ml CH$_2$Cl$_2$ was added slowly. The reaction was monitored by TLC (1:1 hexane/acetone) while adding another 2.5 equivalents (2.7 g) of methyl isocyanate until the reaction was complete. The solution was warmed to room temperature, washed successively with brine (2×100 ml) and water (1×100 ml), dried over Na$_2$SO$_4$ and concentrated. The oil was purified by flash column chromatography using ethyl acetate as the solvent system. 3-(N-Cyclopropyl-N-methylaminocarbonyl)amino-1,2,3,3a,4,8b-hexahydro-4-methylcyclopent[b]indol-7-yl phenylmethylcarbonate was isolated (4.5 g). The material was dissolved in absolute ethanol (190 ml), and 10% palladium on carbon (10% by weight; 0.4 g) was added. The solution was placed in a Parr shaker bottle, charged with H$_2$ (45 psi) and shaken for 2 hours. The catalyst was filtered and the filtrate was concentrated. The oil was triturated with EtOAc (50 ml) and CH$_2$Cl$_2$ (5 ml) to give an off-white solid (1.05 g).

3-(N-Cyclopropyl-N-methylaminocarbonyl)amino-1,2,3,3a,4,8b-hexahydro- 4-methylcyclopent[b]indol-7-ol was characterized by NMR, MS and IR.

The solid (0.8 g) was dissolved in 8:1 Et$_2$O/EtOH (200 ml) initially and ethereal hydrogen chloride was added slowly until the solution became neutral and then more Et$_2$O (800 ml) was added.

3-(N-Cyclopropyl-N-methylamino-carbonyl)amino-1,2,3,3a,4,8b-hexahydro-4-methylcyclopent[b]indol-7-ol hydrochloride was isolated as an off-white solid after filtering and drying under N$_2$ (0.65 g).

| ANALYSIS: | | | |
|---|---|---|---|
| Calculated for C$_{17}$H$_{23}$N$_2$O$_3$.HCl: | 60.44% C | 7.16% H | 12.44% N |
| Found: | 60.77% C | 7.41% H | 12.67% N |

EXAMPLE 30

3-(N-Cyclopropyl)amino-4-methyl-1,2,3,4-tetrahydrocyclopent[b]indol-7-yl methylcarbamate 3-(N-Cyclopropyl)amino-4-methyl-1,2,3,4-tetrahydrocyclopent[b]indol-7-ol (2.2 g) was dissolved in CH$_2$Cl$_2$ (200 ml) with 1,8-diazabicyclo[5.4.0]undec-7-ene (DBU; 0.21 g) and the solution was cooled to 0° C. A solution of methyl isocyanate (0.52 g in 30 ml CH$_2$Cl$_2$) was added slowly to the cooled solution and the reaction was monitored by thin layer chromatography (silica gel, 1:1 hexane/ethyl acetate). After warming to room temperature, the mixture was washed successively with water (2×100 ml), brine (1×100 ml) and again with water (1×100 ml). The organic layer was dried over Na$_2$SO$_4$ and the solvent removed in vacuo. The crude material was recrystallized from acetonitrile. 3-(N-Cyclo-propyl)amino-4-methyl-1,2,3,4-tetrahydrocyclopent[b]indol-7-yl methylcarbamate was isolated as light yellow/white plates (1.0 g).

| ANALYSIS: | | | |
|---|---|---|---|
| Calculated for C$_{17}$H$_{21}$N$_3$O$_2$: | 68.21% C | 7.07% H | 14.04% N |
| Found: | 68.08% C | 6.57% H | 13.97% N |

EXAMPLE 31

1,2,3,3a,4,8b-Hexahydro-4-methyl-3-(N-phenylmethyl-N-methylaminocarbonyl)aminocyclopent[b]indol-7-yl phenylmethylcarbonate To a stirred solution of 1,2,3,3a,4,8b-hexahydro-4-methyl-3-phenylmethylaminocyclopent[b]indol-7-ol (12.0 g) in CH$_2$Cl$_2$ (125 ml) was added triethylamine (4.08 g). The mixture was cooled to 0° C. and a solution of benzyl chloroformate (6.8 g) in CH$_2$Cl$_2$ (50 ml) was added slowly in a dropwise manner. After three hours the reaction mixture was washed with water (2×100 ml), dried over Na$_2$SO$_4$ and concentrated to give 17.0 grams of an oil. The crude 4-methyl-3-(N-phenylmethyl)amino-1,2,3,3a,4,8b-hexahydrocyclopent[b]indol-7-yl phenylmethylcarbonate (17.0 g) was dissolved in CH$_2$Cl$_2$ (125 ml) and 1,8-diazabicyclo[5.4.0]undec-7-ene (0.9 g) was added followed by the dropwise addition of a solution of methyl isocyanate (2.6 g) in CH$_2$Cl$_2$ (25 ml). The reaction mixture was stirred for 2 hours and an additional 0.5 gram of methyl isocyanate was added. The reaction mixture was stirred for an additional 15 minutes and thereafter concentrated in vacuo to give an oil which was purified by flash chromatography on silica gel eluting with 2:1 hexane/ethyl acetate. The product-containing fractions were collected and concentrated to give an oil (5.5 g).

| ANALYSIS: | | | |
|---|---|---|---|
| Calculated for $C_{22}H_{25}N_3O_4$: | 71.73% C | 6.43% H | 8.65% N |
| Found: | 71.67% C | 6.59% H | 8.67% N |

EXAMPLE 32

1,2,3,3a,4,8b-Hexahydro-4-methyl-3-phenylmethoxycarbonylaminocyclopent[b]indol-7-ol A solution of 4-methyl-3-phenylmethylimino-1,2,3,4-tetrahydrocyclopent[b]indol-7-ol (14.0 g) was placed in a 3-neck flask and cooled to 0° C. in an ice-water bath. A solution of 1M borane/THF in THF (145 ml) was added in a dropwise manner. The mixture was stirred for 1 hour while it was slowly warmed to room temperature. The mixture was cooled back to 0° C. and trifluoroacetic acid was added in a dropwise manner. The solution was stirred for 15 minutes, neutralized with 10% NaOH (Aq), extracted with $CH_2Cl_2$, dried ($Na_2SO_4$) and concentrated to give 1,2,3,3a,4,8b-hexahydro-4-methyl-3-phenylmethylaminocyclopent[b]indol-7-ol (14 grams).

20% Palladium hydroxide on carbon (1.4 g) was added to a solution of 1,2,3,3a,4,8b-hexahydro-4-methyl-3-phenylmethylaminocyclopent[b]-indol-7-ol (14 grams) in ethanol (100 ml) and the mixture was hydrogenated at 45 psi $H_2$ pressure using a Parr apparatus at 500° C. for 5 hours. The mixture was filtered and the solution was concentrated to give 3-amino-1,2,3,3a,4,8b-hexahydro-4-methylcyclopent[b]indol-7-ol (10.7 grams).

To a solution of 3-amino-1,2,3,3a,4,8b-hexahydro-4-methylcyclopent[b]-indol-7-ol (10.7 grams) in methylene chloride (125 ml) was added triethylamine (5.6 grams) followed by the dropwise addition of benzyl chloroformate (10.0 grams) in methylene chloride (25 ml). The mixture was stirred for 2 hours, extracted with water, dried ($Na_2SO_4$) and concentrated. The product was purified by chromatography on silica gel, eluting with 2:1 hexane/acetone to provide 1,2,3,3a,4,8b-hexahydro-4-methyl-3-phenylmethoxycarbonylaminocyclopent-[b]indol-7-ol.

EXAMPLE 33

1,2,3,3a,4,8b-Hexahydro-4-methyl-3-(N-phenylmethoxycarbonyl)aminocyclopent[b]indol-7-yl methylcarbamate To a stirred solution of 1,2,3,3a,4,8b-hexahydro-4-methyl-3-(N-phenylmethoxycarbonyl)aminocyclopent[b]indol-7-ol (1.8 g) in $CH_2Cl_2$ (75 ml) was added 1,8-diazabicyclo[5.4.0]undec-7-ene (0.12 g) followed by the dropwise addition of a solution of methyl isocyanate (0.36 g) in $CH_2Cl_2$ (25 ml). The reaction mixture was stirred for 2 hours and an additional 0.1 gram of methyl isocyanate was added. The reaction mixture was stirred for an additional 15 minutes and concentrated in vacuo to give an oil which was purified by flash chromatography on silica gel eluting with 2:1 hexane/ethyl acetate. The product which crystallized from the pure fractions was collected by filtration to give 600 mg and the filtrate was concentrated to give an oil (800 mg) which crystallized upon standing.

| ANALYSIS: | | | |
|---|---|---|---|
| Calculated for $C_{22}H_{25}N_3O_4$: | 66.82% C | 6.37% H | 10.63% N |
| Found: | 66.91% C | 6.47% H | 10.66% N |

EXAMPLE 34

3-Methylaminocarbonyloximino-4-methyl-1,2,3,4-tetrahydrocyclopent[b]indol-7-yl methylcarbamate hemihydrate To a stirred suspension of 3-hydroxyimino-4-methyl-1,2,3,4-tetrahydrocyclopent[b]indol-7-ol (3.0 g) in $CH_2Cl_2$ (100 ml) was added 1,8-diazabicyclo[5.4.0]undec-7-ene (630 mg) followed by methyl isocyanate (1.9 g) and the mixture was stirred overnight at ambient temperature. The mixture was concentrated in vacuo and the resulting solid was recrystallized from ethanol to give 3-methylaminocarbonyloximino-4-methyl-1,2,3,4-tetrahydrocyclopent-[b]indol-7-yl methylcarbamate hemihydrate (1.7 g).

| ANALYSIS: | | | |
|---|---|---|---|
| Calculated for $C_{16}H_{18}N_4O_4$ · $0.5H_2O$: | 56.68% C | 5.66% H | 16.53% N |
| Found: | 56.57% C | 5.46% H | 16.68% N |

EXAMPLE 35

1,2,3,3a,4,8b-Hexahydro-4-methyl-3-methylaminocarbonylaminocyclopent[b]indol-7-ol hydrochloride monohydrate A solution of 1,2,3,3a,4,8b-hexahydro-4-methyl-3-(N-phenylmethyl-N-methylaminocarbonyl)aminocyclopent[b]indol-7-yl phenylmethyl carbonate (1.7 g) in glacial acetic acid (100 ml) was hydrogenated at 45 psi $H_2$ and 50° C. in the presence of 20% Pd hydroxide on carbon utilizing a Parr apparatus. After four hours, TLC indicated a complete reaction with the formation of a major product as well as a side product. The Pd catalyst was filtered under nitrogen and the filtrate concentrated in vacuo. The material was chromatographed on silica gel eluting with 10% $MeOH/CH_2Cl_2$. The product-containing fractions were collected and concentrated. The resulting oil was dissolved in EtOH (25 ml) and $Et_2O$ (150 ml), the solution was filtered, and ethereal HCl was added to the filtrate until the solution became acidic. The colorless solid which formed was collected under $N_2$ and dried under vacuum to give 1,2,3,3a,4,8b-hexahydro-4-methyl-3-methylaminocarbonylaminocyclopent[b]indol-7-ol hydrochloride monohydrate (0.25 g).

| ANALYSIS: | | | |
|---|---|---|---|
| Calculated for $C_{14}H_{19}N_3O_2$ · $HCl.H_2O$: | 53.25% C | 7.02% H | 13.31% N |
| Found: | 53.26% C | 6.54% H | 12.78% N |

EXAMPLE 36

1,2,3,3a,4 8b-Hexahydro-4-methyl-3-(N-phenylmethyl-N-methylaminocarbonyl)aminocyclopent[b]indol-7-ol hydrochloride A solution of 1,2,3,3a,4,8b-hexahydro-4-methyl-3-(N-phenylmethyl-N-methylaminocarbonyl)aminocyclopent[b]indol-7-yl phenylmethyl carbonate (2.0 g) in absolute ethanol (100 ml) was hydrogenated at 45 psi $H_2$ in the presence of 5% Pd-carbon utilizing a Parr apparatus. After two hours, TLC indicated a complete reaction with the formation of a single product. The Pd catalyst was filtered under nitrogen and the filtrate concentrated in vacuo. The resulting oil was dissolved in EtOAc (25 ml) and $Et_2O$ (150 ml), the solution was filtered and ethereal HCl was added to the filtrate until the solution became acidic. The colorless solid which formed was collected under $N_2$ and dried overnight at 40° C. under vacuum to give 1,2,3,3a,4,8b-hexahydro-4-methyl-3-(N-phenylmethyl-N-methylaminocarbonyl)aminocyclopent[b]indol-7-ol hydrochloride (1.4 g).

| ANALYSIS: | | | |
|---|---|---|---|
| Calculated for $C_{21}H_{25}N_3O_2$·HCl: | 65.02% C | 6.76% H | 10.83% N |
| Found: | 64.95% C | 6.85% H | 10.84% N |

EXAMPLE 37

4-Methyl-3-phenylethylimino-1,2,3,4-tetrahydrocyclopent[b]indol-7-ol hemihydrate To a stirred solution of 7-hydroxy-4-methyl-1,4-dihydrocyclopent[b]-3-one (5.0 g) in acetonitrile (100 ml) were added phenethylamine (6.0 g) and titanium isopropoxide (14.1 g), and the resulting mixture was stirred under nitrogen at ambient temperature for 3 hours. The mixture was poured onto ice/water (200 ml) and thereafter, $CH_2Cl_2$ (500 ml) was added. The mixture was filtered, and the organic layer was separated from the filtrate, dried over sodium sulfate and concentrated in vacuo. Crystallization from $CH_2Cl_2$/hexane provided 4-methyl-3-phenylethylimino-1,2,3,4-tetrahydrocyclopent-[b]indol-7-ol hemihydrate (3.0 g).

| ANALYSIS: | | | |
|---|---|---|---|
| Calculated for: $C_{20}H_{20}N_2O\cdot\frac{1}{2}H_2O$ | 76.65% C | 6.75% H | 8.94% N |
| Found: | 76.53% C | 6.38% H | 8.89% N |

EXAMPLE 38

4-Methyl-3-phenylethylimino-1,2,3,4-tetrahydrocyclopent-[b]indol-7-yl methylcarbamate To a stirred solution of 4-methyl-3-phenylethylimino-1,2,3,4-tetrahydrocyclopent-[b]indol-7-ol hemihydrate (1.43 g) in $CH_2Cl_2$ (25 ml) was added 1,8-diazabicyclo[5.4.0]undec-7-ene (0.11 g). Methylisocyanate (0.27) in $CH_2Cl_2$ (20 ml) was added to the reaction mixture. The reaction was monitored by TLC and after 3 hours the $CH_2Cl_2$ was evaporated off. The brown residue was recrystallized from acetonitrile.

| ANALYSIS: | | | |
|---|---|---|---|
| Calculated for: $C_{22}H_{23}N_3O_2$ | 73.11% C | 6.41% H | 11.63% N |
| Found | 73.03% C | 6.35% H | 11.65% N |

EXAMPLE 39

4-Methyl-3-(2-phenylethyl)amino-1,2,3,4-tetrahydrocyclopent[b]indol-7-yl methylcarbamate hydrochloride hemihydrate To a stirred solution of 4-methyl-3-(2-phenylethyl)imino-1,2,3,4-tetrahydrocyclopent[b]indol-7-yl methylcarbamate (0.80 g) in acetic acid (8 ml), ethanol (8 ml), isopropanol (8 ml) and tetrahydrofuran (8 ml) was added sodium cyanoborohydride (0.35 g) under nitrogen. The reaction was monitored by TLC and after 1 hour the solution was neutralized with saturated $NaHCO_3$, extracted with EtOAc, dried over $Na_2SO_4$, and concentrated in vacuo. The resulting yellow oil was dissolved in a minimum amount of EtOAc, diluted with ether and thereafter, an etheral HCl solution was added. The resulting white solid was collected via filtration. Crystallization from ethanol afforded 4-methyl-3-(2-phenylethyl)amino-1,2,3,4-tetrahydrocyclopent[b]indol-7-yl methyl carbamate hydrochloride hemihydrate (0.68 g). The reaction was repeated and the material combined.

| ANALYSIS: | | | |
|---|---|---|---|
| Calculated for $C_{22}H_{25}N_3O_2$·HCl·$\frac{1}{2}H_2O$: | 64.62% C | 6.65% H | 10.28% N |
| Found: | 64.56% C | 6.72% H | 9.91% N |

EXAMPLE 40

4-Methyl-3-(2-propynyl)imino-1,2,3,4-tetrahydrocyclopent[b]-indol-7-yl methylcarbamate To a stirred suspension of 7-hydroxy-4-methyl-1,4-dihydrocyclopent[b]indol-3(2H)-one (5.5 g) in acetonitrile (100 ml) was added propargyl amine (3.0 g), the solution was stirred at room temperature under a nitrogen atmosphere while titanium (IV) isopropoxide (15.6 g) was added in a dropwise manner. The mixture was stirred for 16 hours before quenching with ice water. The mixture was filtered, the solids were washed with $CH_2Cl_2$, the layers were separated and the organic portion was dried ($Na_2SO_4$). After concentration, the crude product was purified via flash chromatography eluting with hexane/acetone (2:1) to give 4-methyl-3-(2-propynyl)imino-1,2,3,4-tetrahydrocyclopent[b]indol-7-ol.

To a stirred solution of 4-methyl-3-(2-propynyl)imino-1,2,3,4-tetrahydrocyclopent[b]indol-7-ol (3.4 g) in $CH_2Cl_2$ (15.0 ml) was added 1,8-diazabicyclo[5.4.0]undec-7-ene (326 mg) followed by the dropwise addition of methyl isocyanate (0.8 g) in $CH_2Cl_2$ (5.0 ml). The reaction was monitored via TLC and after 1.0 hour, the solution was concentrated and the crude product was purified via flash chromatography eluting with hexane/acetone (2:1). The product which precipitated out of the pure fractions was collected to give 4-methyl-3-(2-propynyl)imino-1,2,3,4-tetrahydrocyclopent[b]indol-7-yl methylcarbamate (1.2 grams) and the fractions were concentrated to give an additional 0.9 gram.

| ANALYSIS: | | | |
|---|---|---|---|
| Calculated for $C_{17}H_{17}N_3O_2$: | 69.14% C | 5.80% H | 14.23% N |
| Found: | 68.94% C | 5.81% H | 13.94% N |

EXAMPLE 41

4-Methyl-3-(2-propynyl)amino-1,2,3,4-tetrahydrocyclopent[b]-indol-7-yl methylcarbamate hydrochloride monohydrate To a stirred solution of 4-methyl-3-(2-propynyl)imino-1,2,3,4-tetrahydrocyclopent[b]indol-7-yl methylcarbamate (1:1 g) in acetic acid (10 ml) was added sodium cyanoborohydride (0.57 g). The reaction was monitored via TLC and after 2 hours, methylene chloride (50 ml) was added and the solution was washed with saturated $NaHCO_3$ until neutral. The methylene chloride layer was dried ($Na_2SO_4$), filtered and concentrated. The resulting material was chromatographed on silica gel, eluting with 2:1 hexane/acetone and the pure fractions were collected and concentrated. The resulting solid was dissolved in a minimum amount of EtOAc, diluted with ether and thereafter, ethereal HCl solution was added. The resulting solid was collected via filtration under nitrogen to give 4-methyl-3-(2-propynyl)amino-1,2,3,4,-tetrahydrocyclopent[ b]indol-7-yl methylcarbamate hydrochloride monohydrate (0.4 grams). The reaction was repeated and the products were combined.

| ANALYSIS: | | | |
|---|---|---|---|
| Calculated for $C_{17}H_{19}N_3O_2$. $HCl.H_2O$: | 58.04% C | 6.30% H | 11.94% N |
| Found: | 57.99% C | 6.03% H | 11.82% N |

EXAMPLE 42

4-Methyl-3-(2-phenylethyl)amino-1,2,3,4-tetrahydrocyclopent[b]-indol-7-yl phenylmethylcarbamate hydrochloride hemihydrate To a stirred solution of 4-methyl-3-(2-phenylethyl)imino-1,2,3,4-tetrahydrocyclopent[b]indol-7-ol (2.70 g) in $CH_2Cl_2$ (100 ml) was added 1,8-diazabicyclo[5.4.-0]undecene (0.21 g). Benzyl isocyanate (0.83 g) was added to the reaction mixture via a syringe and the mixture stirred under nitrogen. Additional benzyl isocyanate was added after 120 and 180 minutes in ¼ and ½ equivalents, respectively. The reaction was monitored by TLC and after 185 minutes the solution was concentrated in vacuo. The crude reaction residue (2.72 g) showed carbamate formation according to proton NMR and MS. The residue was dissolved in glacial acetic acid (75 ml) with stirring under nitrogen. A yellow precipitate formed upon addition of sodium cyanoborohydride (0.98 g) and dissolved after 30 minutes. One equivalent of sodium cyanoborohydride was added after 3 hours. After 30 minutes, TLC showed complete reaction. The reaction mixture was neutralized with saturated sodium bicarbonate solution, extracted with ethyl acetate, dried over $Na_2SO_4$, and concentrated in vacuo. The free base was dissolved in ether and an ethereal solution of HCl was added. The resulting white solid was collected via filtration.

| ANALYSIS: | | | |
|---|---|---|---|
| Calculated for $C_{28}H_{30}N_3O_2$. $HCl.\frac{1}{2}H_2O$: | 69.34% C | 6.44% H | 8.66% N |
| Found: | 69.45% C | 6.30% H | 8.72% N |

EXAMPLE 43

4-Methyl-3-[2-(4-morpholinyl)ethyl]imino-1,2,3,4-tetrahydrocyclopent[b]indol-7-ol To a stirred solution of 7-hydroxy-4-methyl-1,4-dihydrocyclopent[b]indol-3-one (8.00 g) in acetonitrile (125 ml) under nitrogen were added 4-(2-aminoethyl)morpholine (10.35 g) and titanium isopropoxide (22.60 g). The reaction was monitored by TLC and after two hours additional equivalents of 4-(2-aminoethyl)morpholine (5.17 g) and titanium isopropoxide (1 1.30 g) were added. Fourteen hours later the reaction was quenched with water (200 ml). EtOAc (200 ml) was added and the mixture stirred for fifteen minutes and filtered. The layers were separated, the aqueous layer was extracted with ethyl acetate, and the combined organics were dried ($Na_2SO_4$) and concentrated in vacuo. The resulting yellow solid was dried yielding 6.65 g. of product. A 2 g sample of the solid was further purified by crystallization from $CH_2Cl_2$/hexane to afford 1.2 g of 4-methyl-3-[2-(4-morpholinyl)ethyl]imino-1,2,3,4-tetrahydrocyclopent[b]indol-7-ol.

| ANALYSIS: | | | |
|---|---|---|---|
| Calculated for $C_{18}H_{23}N_3O_2$: | 68.98% C | 7.40% H | 13.41% N |
| Found: | 68.78% C | 7.52% H | 13.26% N |

We claim:
1. 4-Methyl-3-(2propynyl)amino-1,2,3,4-tetrahydrocyclopent[b]-indol-7-yl methylcarbamate.
2. 1,2,3,3a,4,8b-Hexahydro-4-methyl-3-(N-phenylmethoxycarbonyl) aminocyclopent[b]indol-7-yl methylcarbamate.
3. 1,2,3,3a,4,8b-Hexahydro-4-methyl-3-(N-phenylmethyl-N-methylaminocarbonyl)aminocyclopent[b]indol-7-yl phenylmethylcarbamate.

* * * * *